United States Patent
Bonne et al.

(10) Patent No.: US 6,322,247 B1
(45) Date of Patent: Nov. 27, 2001

(54) MICROSENSOR HOUSING

(75) Inventors: Ulrich Bonne, Hopkins, MN (US); Michael J. Haji-Sheikh, Richardson, TX (US); Robert E. Higashi, Shorewood; Aravind Padmanabhan, Plymouth, both of MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/368,621

(22) Filed: Aug. 5, 1999

Related U.S. Application Data

(63) Continuation-in-part of application No. 09/239,125, filed on Jan. 28, 1999.

(51) Int. Cl.[7] ............................. G01K 1/08; G01K 13/02; G01F 1/684
(52) U.S. Cl. ......................... 374/138; 374/208; 374/147; 73/204.21; 73/204.22
(58) Field of Search ..................................... 374/138, 147, 374/135, 208; 73/866.5, 202, 202.5, 204.21, 204.22, 204.26

(56) References Cited

U.S. PATENT DOCUMENTS

| | | | |
|---|---|---|---|
| 4,184,934 | 1/1980 | Bode et al. ........................ 204/428 |
| 4,208,266 | 6/1980 | Auman et al. ..................... 204/410 |
| 4,744,246 * | 5/1988 | Busta ................................ 73/204.26 |
| 5,014,552 * | 5/1991 | Kamiunten et al. ............... 73/204.21 |
| 5,056,362 * | 10/1991 | Ang et al. ......................... 73/204.26 |
| 5,081,866 * | 1/1992 | Ochiai et al. ..................... 73/204.21 |
| 5,187,674 * | 2/1993 | Bonne ............................... 73/204.26 |
| 5,220,830 * | 6/1993 | Bonne ............................... 73/204.21 |
| 5,249,462 * | 10/1993 | Bonne ............................... 73/204.21 |
| 5,279,155 * | 1/1994 | Johnson et al. ................... 73/202.5 |
| 5,303,167 * | 4/1994 | Bonne ............................... 73/204.26 |
| 5,311,477 * | 5/1994 | Rastegar ........................... 365/230.05 |
| 5,452,621 * | 9/1995 | Aylesworth et al. ............. 73/864.81 |
| 5,505,073 * | 4/1996 | Gerblinger et al. .............. 73/31.05 |
| 5,511,428 * | 4/1996 | Goldberg et al. ................ 73/777 |
| 5,581,038 * | 12/1996 | Lampropoulos et al. ........ 73/727 |
| 5,599,584 * | 2/1997 | Champney, Jr. ................. 427/245 |
| 6,178,811 * | 1/2001 | Bonne et al. .................... 73/54.04 |
| 6,184,773 * | 2/2001 | Bonne et al. .................... 73/204.25 |

FOREIGN PATENT DOCUMENTS

10413 * 1/1982 (JP).

OTHER PUBLICATIONS

Stemme, G., "Micro fluid sensors and actuators", Micro Machine and Human Science, 1995. MHS '95., Proceedings of the Sixth International Symposium on, pp. 45–52, 1995.*

Evans et al., "Planar Laminar Mixer", Micro Electro Mechanical Systems, MEMS 97, Proceedings, IEEE., Tenth Annual International Workshop on MEMS, Jan. 26–30, 1997, pp. 96–101, 1997.*

Holm et al., "Stability and Common Mode Sensitivity of Piezoresitive Silicon Pressure Sensors made by Different Mounting Methods", IEEE., pp. 978–981, 1991.*

* cited by examiner

Primary Examiner—John Barlow
Assistant Examiner—Stanley J. Pruchnic, Jr.
(74) Attorney, Agent, or Firm—John G. Shudy, Jr.

(57) ABSTRACT

A microsensor housing having a structure with at least one inlet at one end and a thermal property sensor at the other end. Situated between the inlet and the sensor is a convection shield. Sampled fluid is taken in the inlet from a channel carrying the fluid to be sampled. The convection flow lines of the fluid are barred by the convection shield. The fluid is diffused into a cavity between the shield and sensor. The sensor detects a thermal property of the diffused fluid. One preferred shield has holes about its perimeter with a solid center part of the shield covering at a distance the sensor. The channel carrying the fluid may have screens to reduce turbulence noise and to aid in fluid transport to and from the sensor housing.

21 Claims, 28 Drawing Sheets

27

MICROSENSOR HOUSING

This application is a CIP of Ser. No. 09/239,125 filed Jan. 28, 1999.

BACKGROUND

The invention relates to fluid sensors and particularly to microsensors. More particularly it pertains to housing for such sensors. Microsensors have one vexing packaging problem. Their space-saving and cost-saving smallness in surface area and membrane thickness make them vulnerable to occasional impacts with particles. The solid particles may destroy the gas-sensitive membrane of the sensor or change its heat transfer features with just a thin coat of sticky particles. The liquid ones may have the same effect as the small solids, if a residue stays after re-evaporation.

These problems continue to be of concern in relation to the development of microsensors of fluid vapor as needed for control or recovery operations of such vapors. The cause of the problem is the need to satisfy two competing goals which are to achieve a short response time (e.g., one to three seconds or less) and a service life of about ten years. Resolving the fundamental approach to sensing fluid properties is an important and essential step. But at least of equal importance is the design of a sensor housing or package, which will enable the sensor to perform its function rapidly, sensitively and reliably, even in harsh environments. The problem is that the filters and baffles one would provide to insure protection for long and reliable sensor service are the same that would increase response time to unacceptable levels. The present invention provides a solution and tradeoff between speed of response and sensor protection.

SUMMARY OF THE INVENTION

The present microsensor housing both protects small, one micrometer-thick sensing structures of thermal microsensors, and facilitates rapid and reliable operation in spite of exposure to forced convection, flow turbulence, dust, droplets and/or condensation.

In order to sense fluid (i.e., gas or liquid) thermophysical properties such as thermal conductivity, specific heat, or its derivatives of oxygen demand, heating value, compressibility factor or octane number, the sensor needs to be in contact with the fluid and be able to reliably sense small changes in the above properties. The sensitivity is provided by the design of the sensor as a chip, featuring low mass, large surface-to-volume ratio heating and sensing elements. Long and reliable service requires that the sensor be protected from interference due to settling dust or droplets, as well as from flow (laminar or turbulent). Protection against condensation means that the sensor is designed to recover its sensing performance within a specified short time after coming in contact with liquid condensates. Rapid response means that the sensor chip itself needs to respond quickly to changes in the fluid properties, as well as that the sensor housing needs to allow quick transport and replacement of "old" with "new" fluid sample elements, without noticeable thermal disturbance due to forced convection or turbulence.

For a fluid property sensor to meet a specified microsensor performance in terms of response time, insensitivity to flow, and service life, aspects of four parameter groups, which a designer can adjust to meet the desired sensor performance, include sensor chip design and performance, geometry of the convective transport section of the sensor housing, geometry of the convective barrier, and geometry of the diffusion transport section.

For the parameters of this tool kit, there are generic as well as quantitative guidelines for the design of microenvironmental protection of (thermophysical property) microsensors, to meet conflicting performance demands for "fast response", "operability in high flows" and "long, reliable service" in harsh field environments. These were characterized by their average dust loads, occasional condensation, maximum flow velocities and flow turbulence, which had resulted in slow response time problems before, due to excessive protection. As a result of this invention, the specifying of performance (response time and service life), and the characterizing of environmental conditions, a microsensor housing for both property sensors and flow sensors has been developed which enables the packaged sensor to meet the desired performance and lifetime specifications.

The proposed approach is shown in FIGS. 4c and 4e. The single-stage baffle is shaped to facilitate liquid runoff via the sides, if liquid should get near the sensor chip. It is machined with a set of concentric holes projecting an area around the chip and inhibiting direct splashes from the direction of the fitting to hit the chip. It provides chip protection while allowing diffusional access of fluid to the chip from all sides.

In summary, the disclosed housing for microsensors features a new environmental protection design based on a single-stage, concentric baffle with openings arranged around the protected sensor. It minimizes remaining dead spaces around the sensor (to reduce response time) by filling-in those spaces that are non-essential for fluid diffusion.

There are advantages of the invention relative to prior art screens and non-concentric baffles. It can be machined in one piece. Its baffle does not need assembly after machining. The concentric baffle holes are large enough to make the probability of clogging negligible. The response time is five to nine times smaller than that measured with a previous 2-stage, non-concentric baffle (having two offset and opposed D-shaped louvers of FIG. 1b). The housing orientation relative to external flow direction does not affect the baffle's effectiveness. It is easy to machine, requires no assembly, and barely increases microsensor response time relative to not having a baffle at all.

BRIEF DESCRIPTION OF THE DRAWING

FIG. 9 reveals results of more droplet testing like that of FIG. 8a.

FIG. 13c shows an expanded end view of a honeycomb flow straightener as shown in FIG. 13a.

DESCRIPTION OF THE EMBODIMENT

Figure 1A:
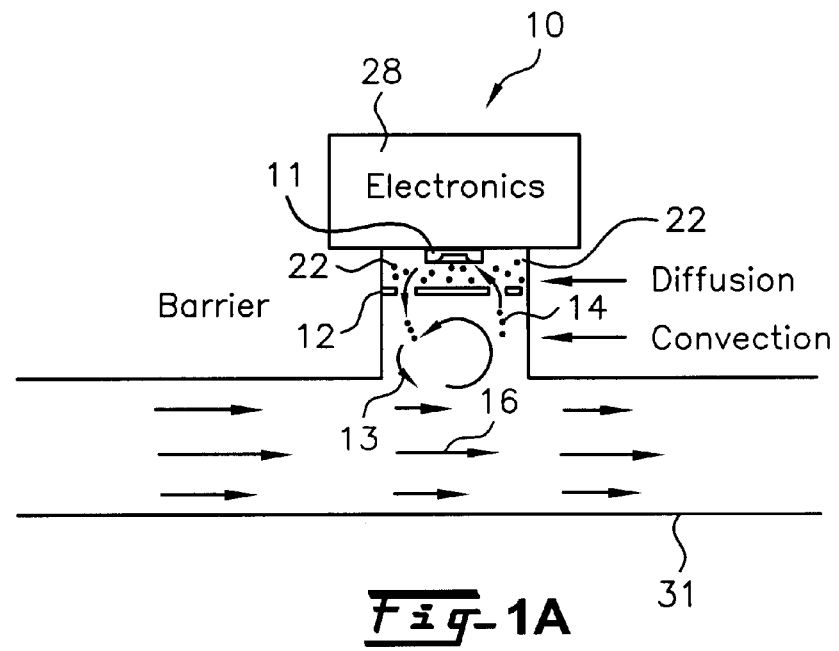
FIGS. 1a and 1b illustrate various aspects of microsensor housing configurations.

Solutions conceived and implemented to date, may either only provide partial protection and clog after a relatively short service life (screens, FIG. 1a) or provide good protection but require costly machining and assembly, and increase response time unacceptably (baffles), see FIGS. 1a and b.

Good sensor protection against dust, vapor mist/gum residue could be achieved with a double or triple screen; but this would increase response time well beyond the specified time. An insertable 2-stage baffle (in the shape of two offset Ds, see FIG. 1b) was found to provide good protection against 1.6 mg droplets (which is not true for the screen) and even against a fine jet of droplets, but had a response time greater than fifteen seconds.

As shown in FIG. 1a, the sensor housing or package 10 solves harsh environmental problems by providing a sensor 11 with a "microenvironmental" shield 12, such that forced convection 13 can transport the fluid sample (with dust and droplets) 14 to shield 12. Then diffusivity transports sample 14 between shield 12 and sensor 11. FIG. 1a shows the principle of housing indicating the protected location of the sensor 11 (its magnified cross section is shown in FIG. 1c), a generic barrier (such as a screen) shield 12 for protection from convection flows, and transport of fluid sample elements 14 to sensor 11 into a diffusion area 22.

Figure 1B:
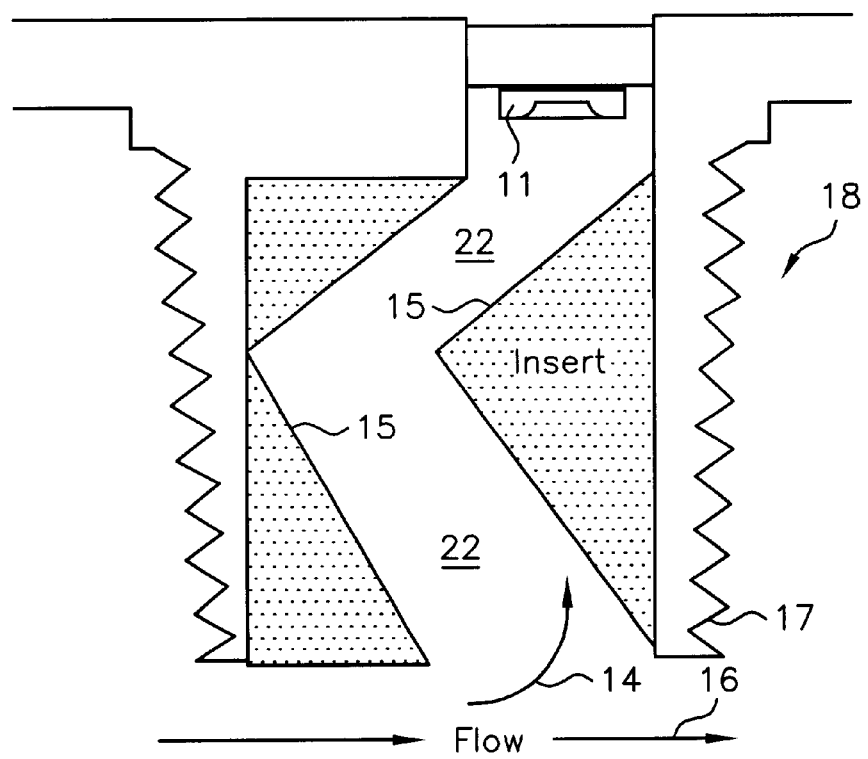

FIG. 1b shows another barrier 15 for a sensor 11, based on an angled path, which avoids a direct line-of-flight between an aerosol from the main flow stream 16 and sensor 11, and an incidental ¼" NPT fitting 17 to attach sensor 18 to the fluid stream to be monitored.

Figure 2:
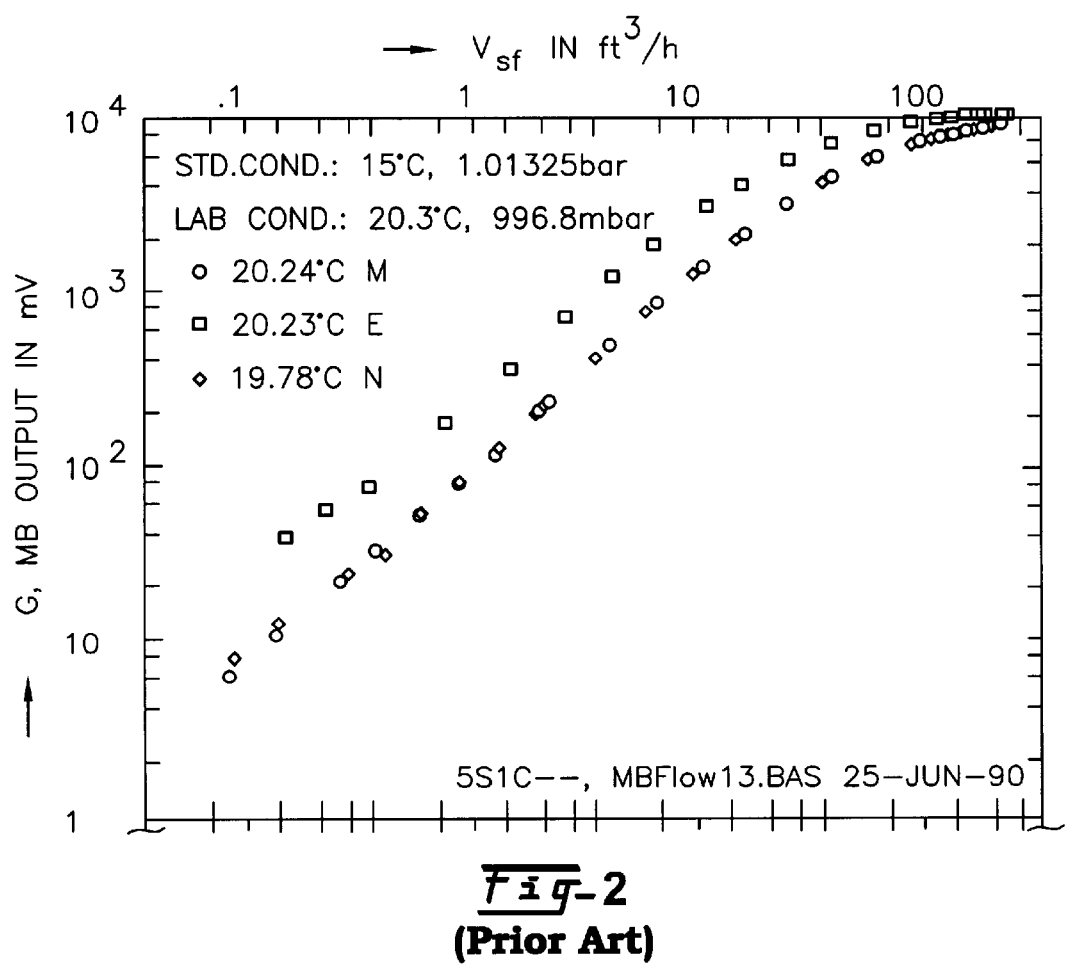
FIG. 2 is a graph of microbridge sensor output versus standard flow for three gases.
Figure 3:
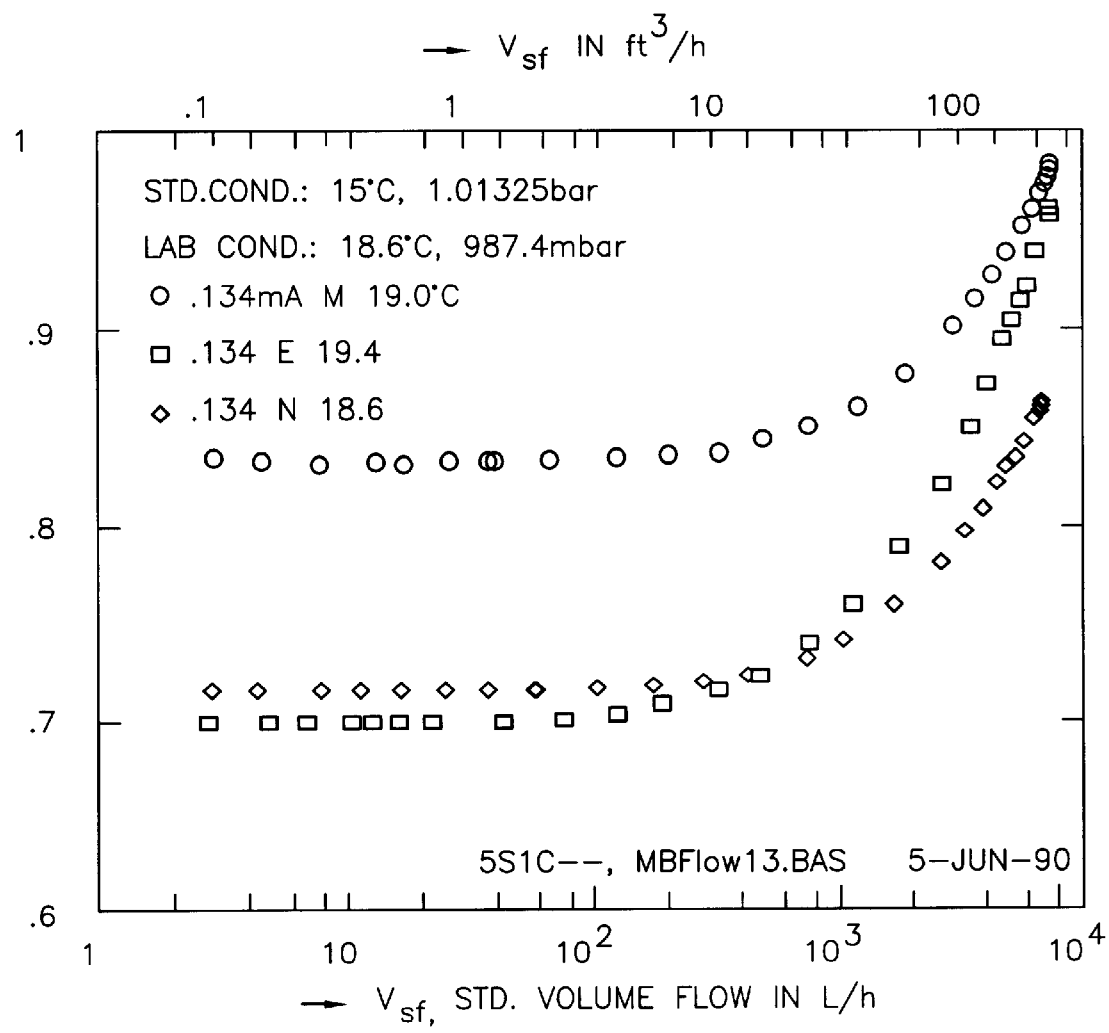
FIG. 3 is graph of microbridge heater power versus standard flow for three gases.

The rationale for housing 18 was derived from measurements, shown in FIGS. 2 and 3, which display microsensor flow data based on two methods of measurement, namely, differential and absolute flow sensing, using the same sensor, whereby the heater is controlled to operate at a constant temperature rise above ambient of about 100 degrees Celsius (C), unless indicated otherwise. In FIG. 2, the flow signal is derived from the difference in temperature between the two non-energized (Pt thin-film resistor) sensing elements flanking the central heating element, all of which are more or less influenced by forced convection. But FIG. 3 shows that this influence is delayed for the heater, which consumes a steady power of about 5 mW within ±0.5% until flow has risen to about 160 L/h, which for the used Venturi nozzle of a 14 mm inside diameter (ID) is equivalent to 28 cm/s. FIG. 3 shows that this heater power is proportional to thermal conductivity, as we compare the data for $CH_4$, $C_2H_6$ and $N_2$, labeled M, E, and N in FIGS. 2 and 3. The plotted heater power, P, can be used to derive thermal conductivity, k, with a linear relationship between heater power and k.

Figure 1C:
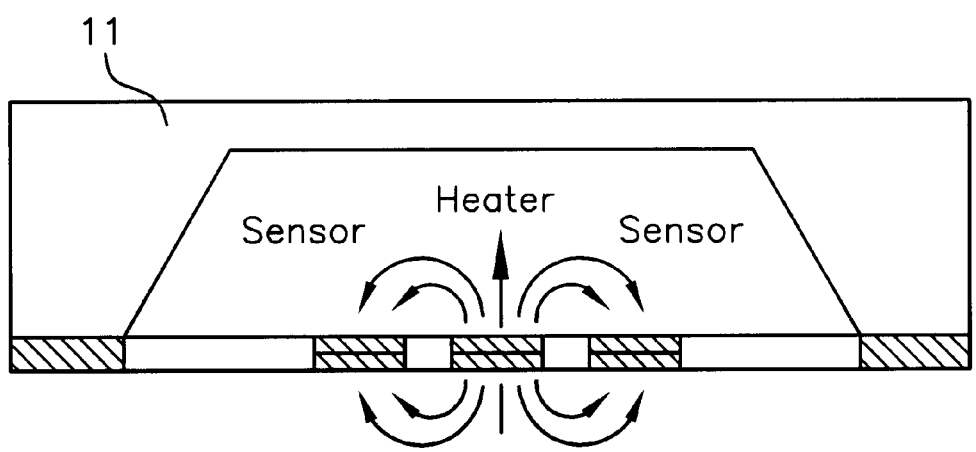
FIG. 1c illustrates a microsensor configuration of the prior art.

Typical industrial gas streams range well above the above value of 28 centimeters per second (cm/s), so that some protection of sensor 11 as indicated in FIGS. 1a–1c is needed. Examples are: 1) 690 cm/s for 250 ft³/h of gas in a ¾" ID pipe to a gas meter, Reynolds number (Re)=9,117; 2) 500 cm/s for 10 gal/min of air in a ½" ID pipe, Re=4,387; 3) 2740 cm/s for 4 kg/min in a 2" ID pipe, Re=96,585; and 4) 2716 cm/s for 200 L/min in a ½ ID pipe, Re=23,551. Although these examples are for individual and unrelated applications, one can derive some generic conclusions and guidelines regarding flow turbulence. The indicated values of the Reynolds number (Re=d·v·ρ/η) fall into the turbulent flow regime of Re>2200, so that one can expect related interferences to show up during fluid property measurements, unless their effect is mitigated.

Figure 4A:
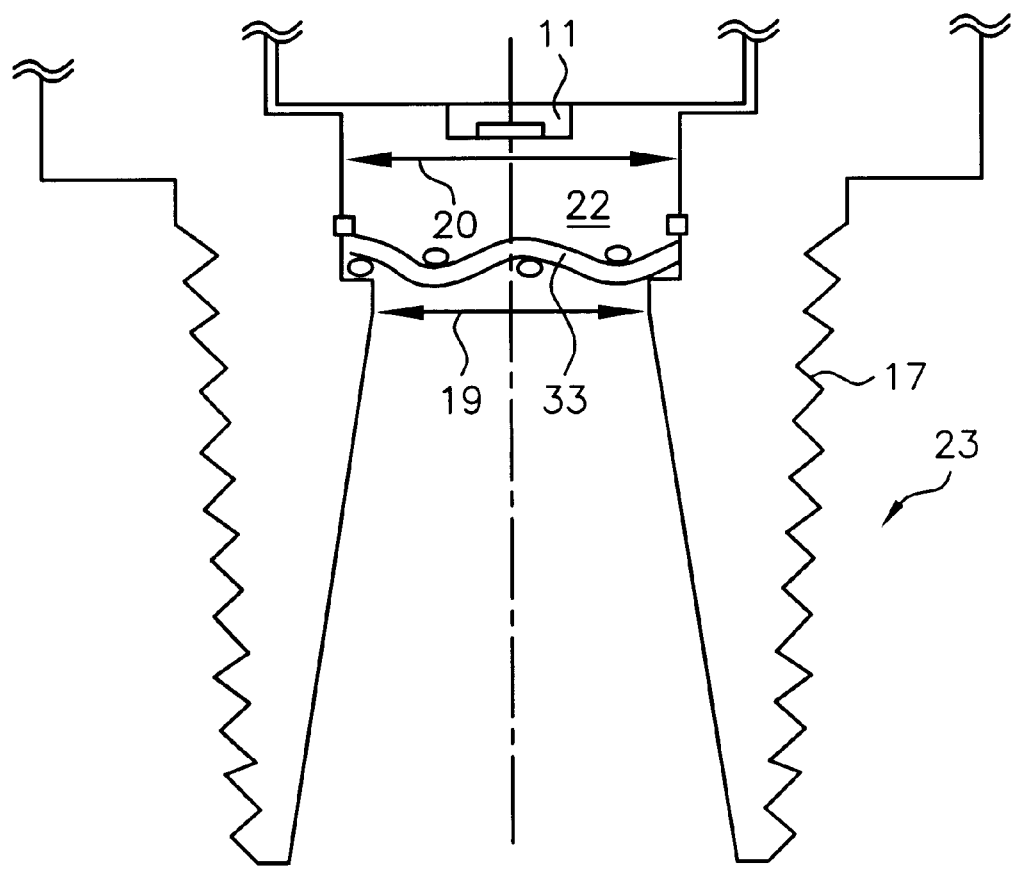
FIGS. 4a–4e are views of microsensor housing designs and layout.
Figure 4B:
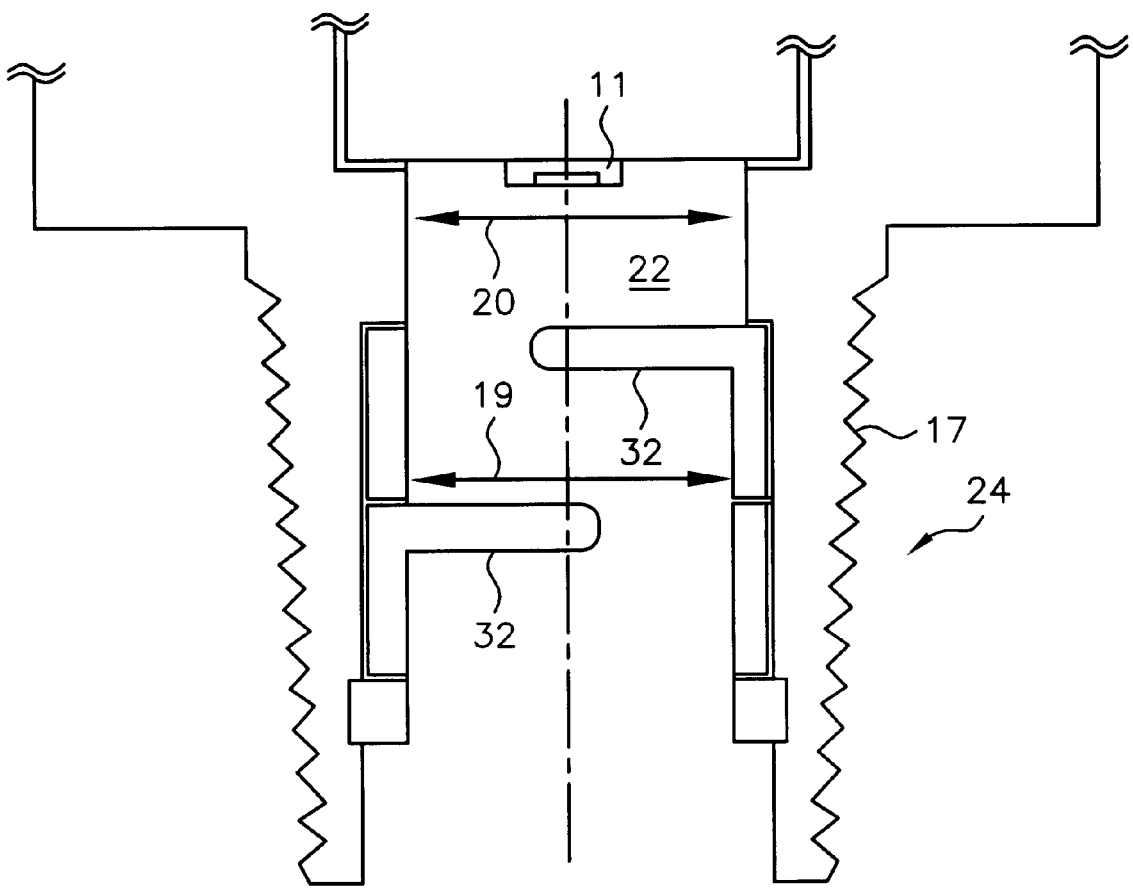
Figure 4C:
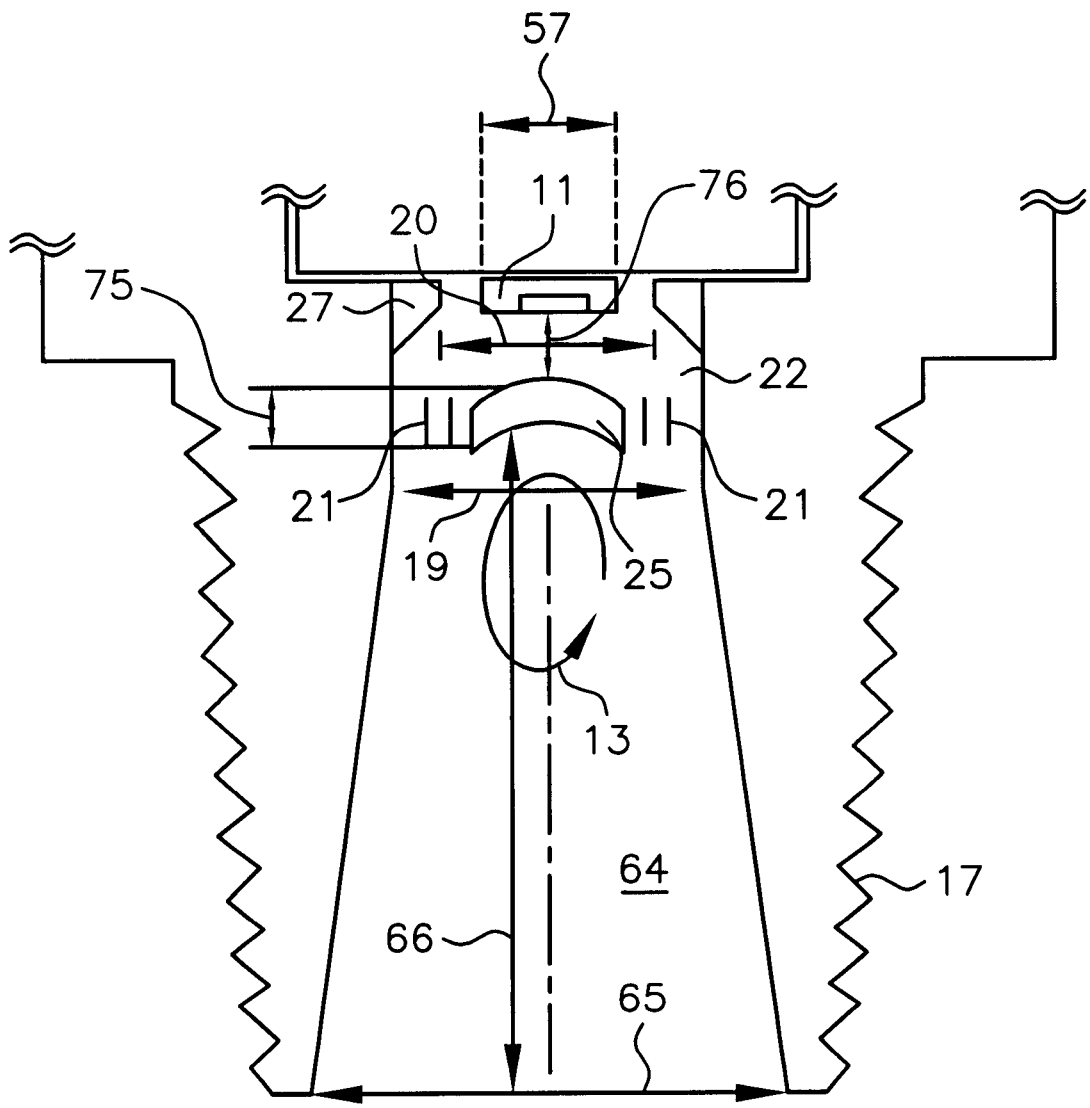
Figure 4D:
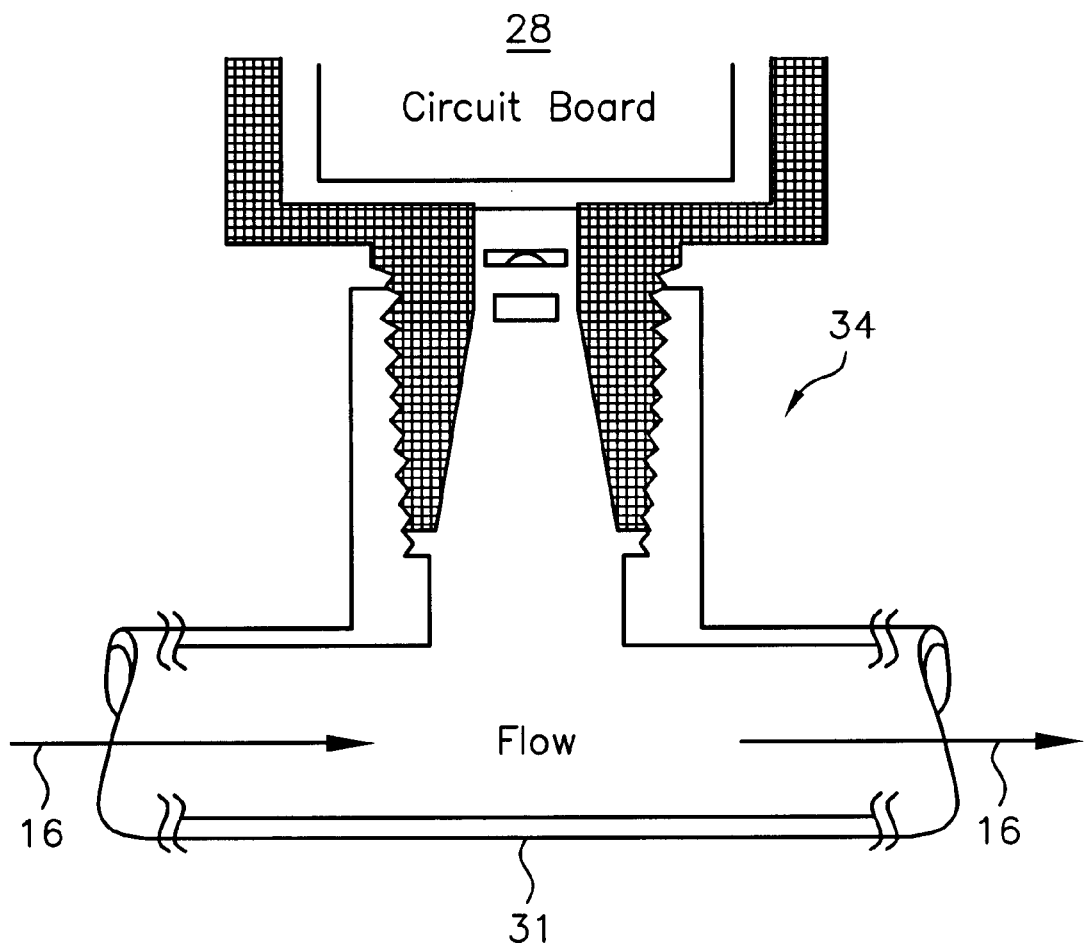
Figure 5A:
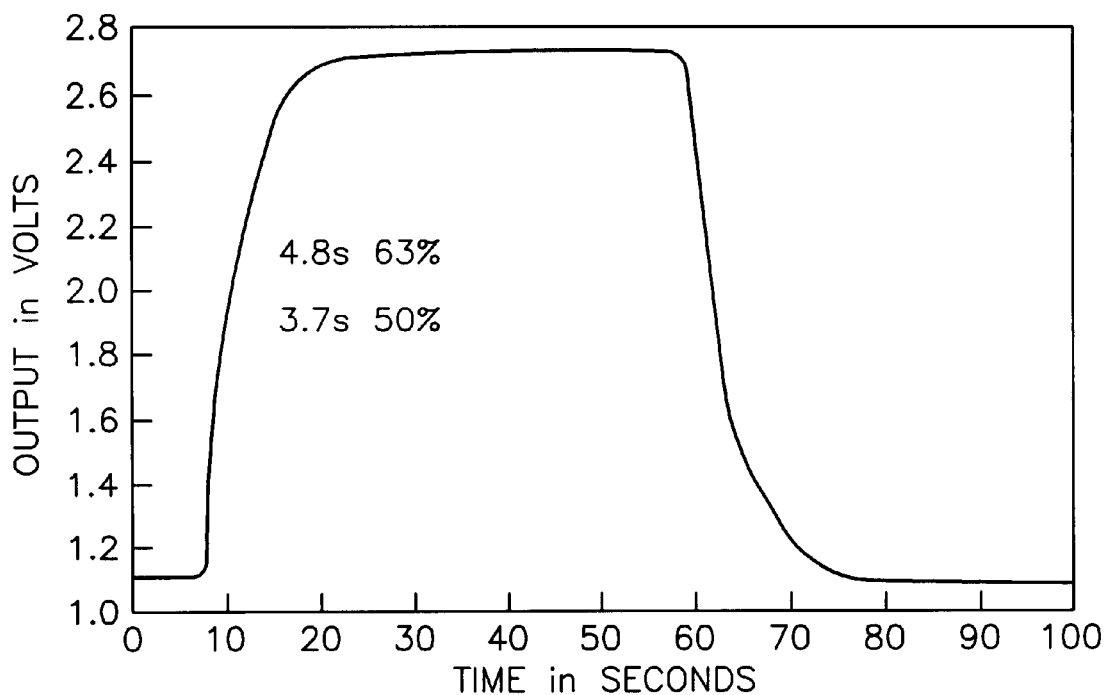
FIGS. 5a–5c are graphs of responses of the sensor with optimal baffle protection for various flow conditions.
Figure 5B:
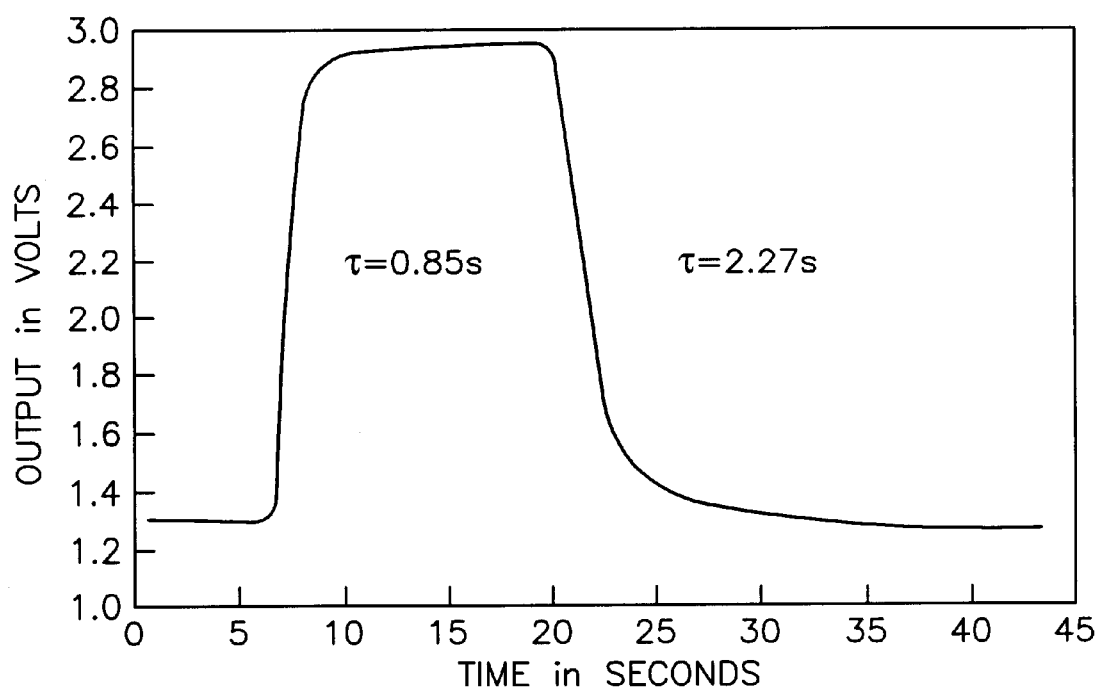
Figure 5C:
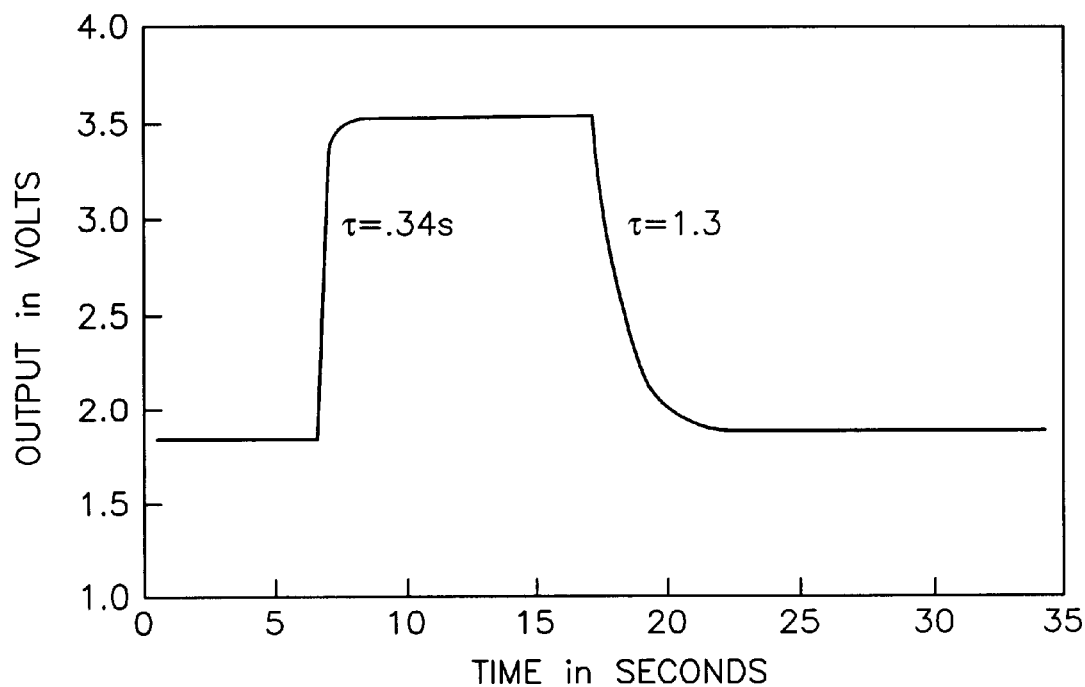
Figure 6A:
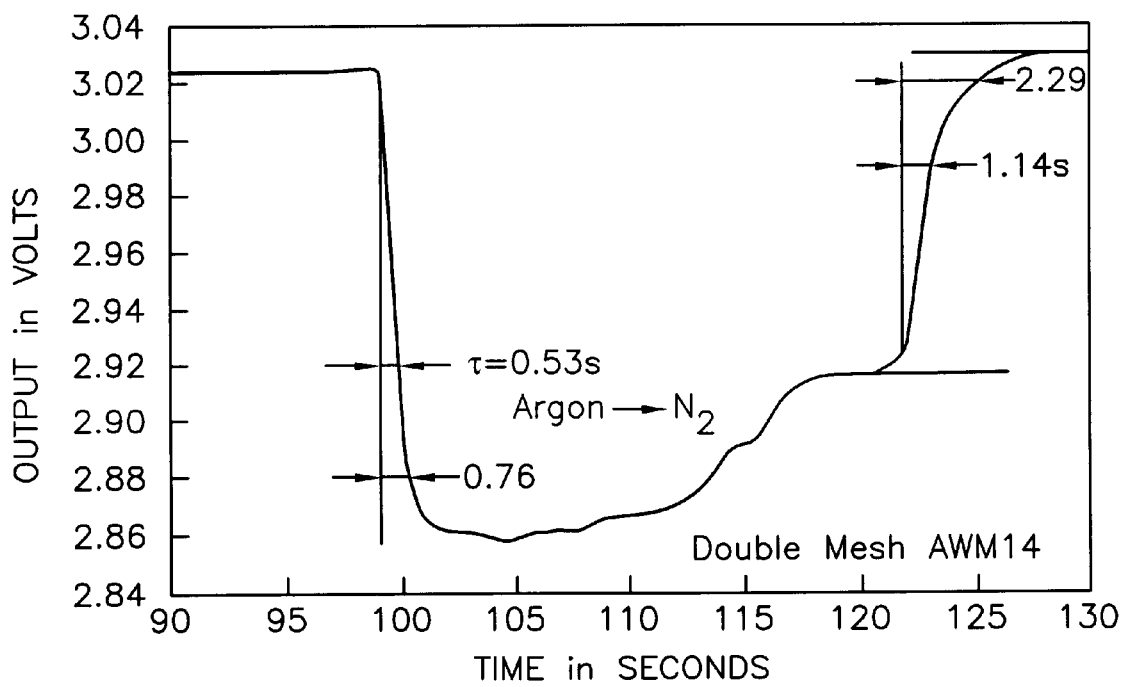
FIGS. 6a–6c show various response times of the sensor for three different gases.
Figure 6B:
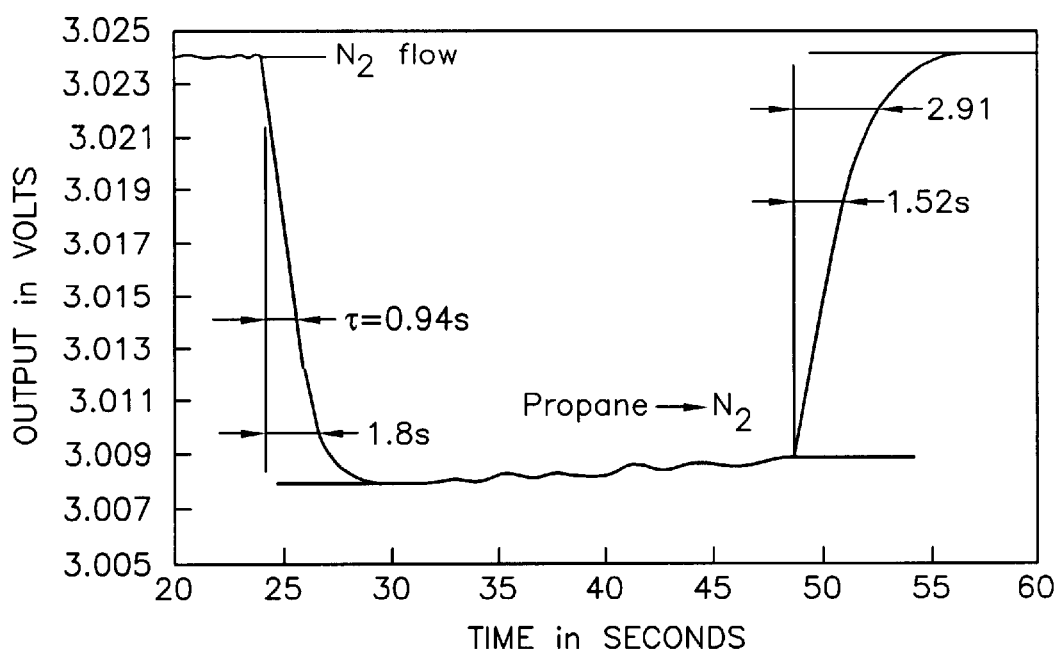
Figure 6C:
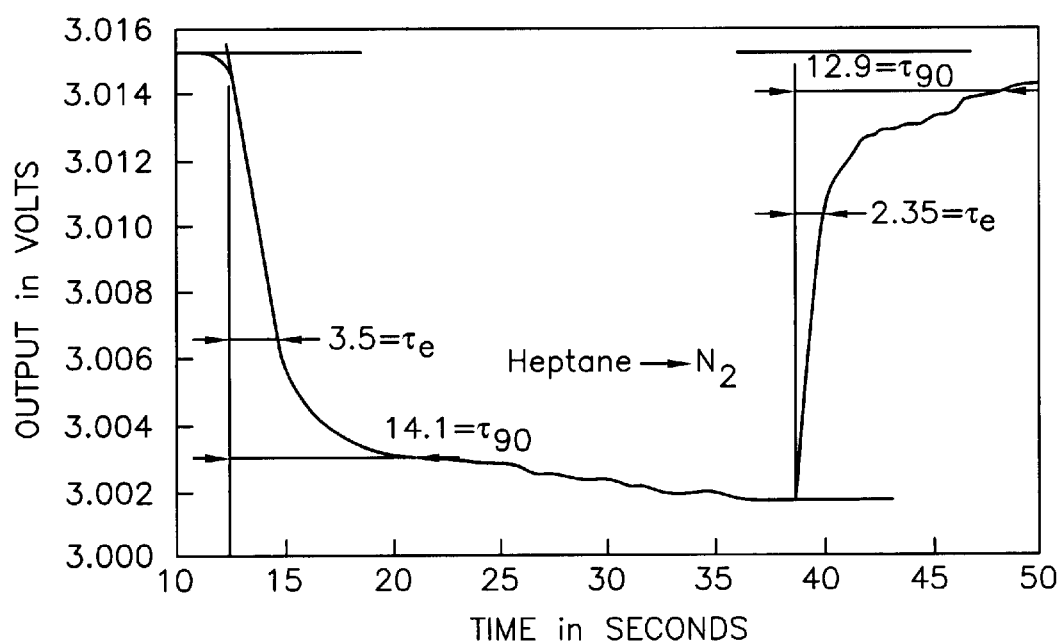

Response times, τ (63 percent), can be and were measured by recording the transient sensor signals during a switch from one gas to another and back (typically from $N_2$ to Ar or to $CH_4$), while maintaining a flow of 240 Liters/hour (about 1 gallon/minute) in a pipe of 18 mm (0.71") ID, corresponding to a linear speed of 26.2 cm/s, and with the sensor chip positioned a distance of 24 mm (0.94") away from the pipe center, as in FIG. 4d. As shown in FIG. 5a, the 240 L/h or 4 L/min requirement was needed to obtain a conservative measure of the response time because under our conditions it was found to decrease somewhat inversely proportional to flow speed. FIGS. 5b and 5c show the effects of flow rates of 600 and 1000 L/h, respectively. As expected from differences in diffusivity values for different gases, FIGS. 6a, 6b and 6c show that gas composition also has an influence on the response time. The response times were observed to increase as the $N_2$-to-gas switch was made with argon, propane and heptane, from 0.53, 0.94 and 3.5 seconds, respectively. And these increases approximately scale as the inverse of their mass diffusivities of 0.096, 0.039 and 0.016, respectively.

To develop a rapid way to estimate the diffusion part of the response time for the design of the housing represented by FIG. 4c, one started with the classical one-dimensional diffusion equation for the effective distance of transport by diffusion, $x^2=2 \cdot D \cdot t$. But rather than pursuing a 3D integration approach for the three-dimensional case, an easy-to-apply diffusional viewing angle approach was developed. This consisted of factoring the ratio of areas of the open part (total area of holes) of the barrier diameter 19 (best shown in FIG. 4f) to the cavity diameter 20 on the opposite end of the cavity toward sensor 11. Together with the convective part of the response time being proportional to the flow velocity, one is able to confirm and predict the response times, τ, for the sensor test configurations 23, 24 and 100 depicted in FIGS. 4a, 4b and 4c, respectively.

Figure 4E:
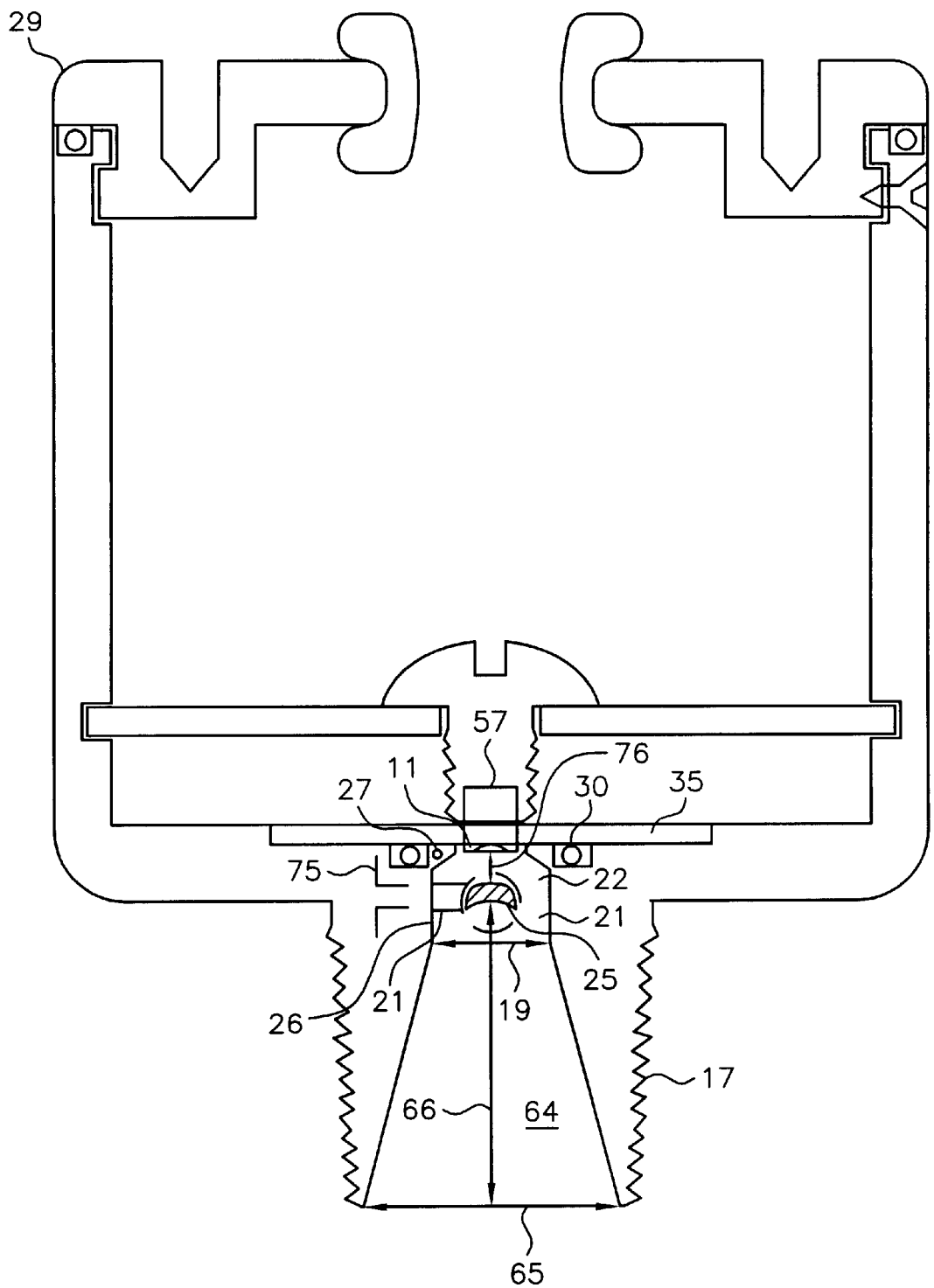
Figure 4F:
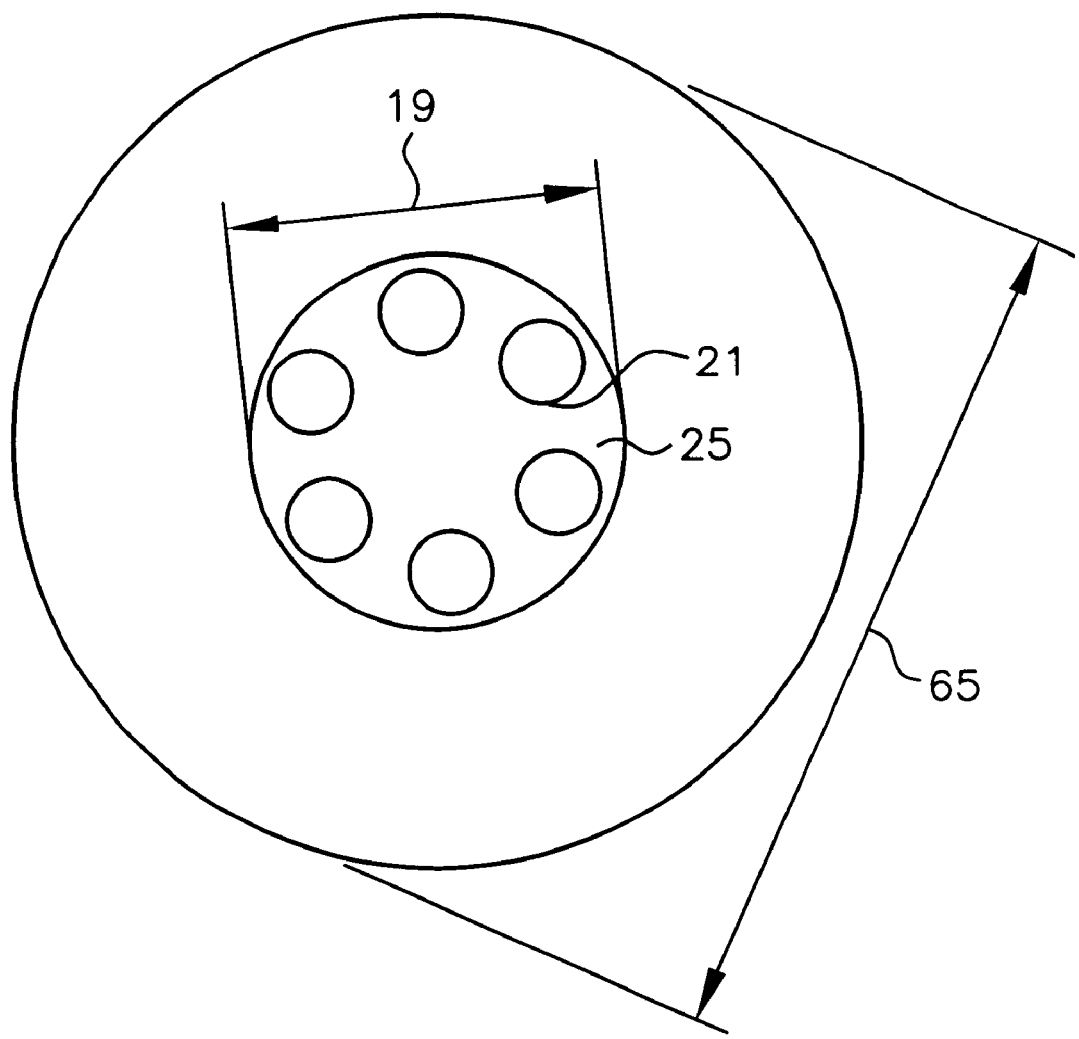
FIG. 4f is a cross-sectional view of a baffle.
Figure 4G:
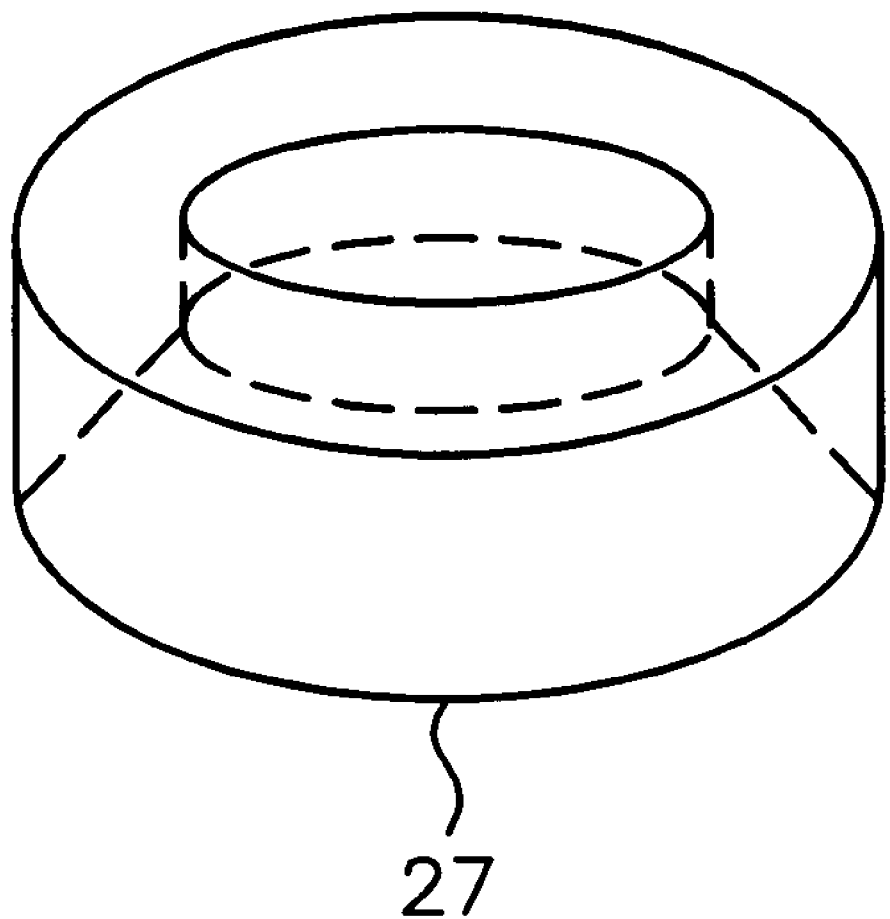
FIG. 4g is an expanded view of a ring-shaped insert.

The approach of the invention is shown in FIGS. 4c and 4e. A single-stage baffle 25 is shaped to facilitate liquid runoff via sides 26, if liquid should get near the sensor 11. Second, it is machined with a set of concentric holes 21 projecting an area around sensor 11 and inhibiting direct splashes from the direction of the fitting to hit sensor 11. Baffle 25 also provides chip protection while allowing diffusional access of fluid to sensor 11 from all sides. A ring-shaped insert 27 reduces the dead space around sensor 11, which may be further cut by means of an epoxy-fill. Insert 27, as shown in FIGS. 4c, 4e, and 4g in expanded view, has an outside diameter of about 0.170 inch, an inside diameter of about 0.130 inch. It has a thickness of about 0.045 inch at the outside diameter and a thickness of about 0.015 inch at the inside diameter. The change in thickness is a straight-line slope from the outside diameter to the inside diameter, with the sloped surface towards baffle 25. An inlet 64 of fitting 17 has a diameter 65 that tapers down to a diameter 19 through the length of the inlet. Baffle 25 is at a distance 66 from the inlet entrance of diameter 65. For certain favorable performance, a ratio of diameter 65 to distance 66 is close to or greater than one.

Referring now jointly to FIGS. 1a and 4c, baffle 25 is a little curved or convex. It is the barrier of convection lines 13 of flow. Shield 12, and/or baffle 25 hinders flow lines 13 of convection. After shield 12 or baffle 25, in the space between the baffle and the sensor, diffusion of fluid 22 takes over the transport job. Baffle 25, or shield 12, as the case may be, keeps the convection of the fluid from sensor 11. Brownian motion takes place between baffle 25, shield 12 and sensor 11. The droplet 39 test shown in FIG. 8b applies to gas. A liquid 38 is the source of saturated vapor in volume 37, which condenses to droplets 39 which are prevented from impinging sensor 11 by the solid area of baffle 25. For supersonic flows, the hole or holes 21 of the baffle 25 would be very small. Baffle 25 center of solid material should mirror the sensor 11 configuration or area. Hole 21 length dampens convection. The length-to-diameter ratio of each hole 21 should not exceed one, that is, $L/D \leq 1$ or $D/L \geq 1$. Hole 21 walls create friction to inhibit convection. The projected volume under the hole 21 area, between the baffle and the sensor, should be about the same as the projected volume under the solid area of baffle 25 between the baffle and sensor. Holes 21 should be small enough to prevent passing of convection of the fluid, and the sum of the projected volumes from holes 21 to the sensor 11 side should be no smaller than the projected volume of the solid part of baffle 25.

Thermal properties include thermal conductivity, specific heat, and thermal diffusivity. The distance between baffle 25 and the sensor 11 surface is kept greater than 100 microns, so as to prevent the quenching the thermal process to be measured. The aspect ratio of the diameter to length of each hole 21 should be close to one for good response time ($D/L \geq 1$). Structure 17 is coned at the input. The sensor 11 recess volume 22 is kept as small as possible to minimize diffusion times. The ratio of sensor 11 diameter 57 to the recess diameter 19 should be close to one but to allow for baffle openings. The area over or under the sensor itself should have no holes 21 or openings in the baffle 25.

The response times of sensors with protection according to FIGS. 4a and 4b are shown in FIGS. 5a, 5b and 5c. Additional acceptance criteria are the sensitivity of the output signal to flow velocities outside of the ¼" NPT fittings 17, and the long term signal drift due to soiling.

Figure 7:
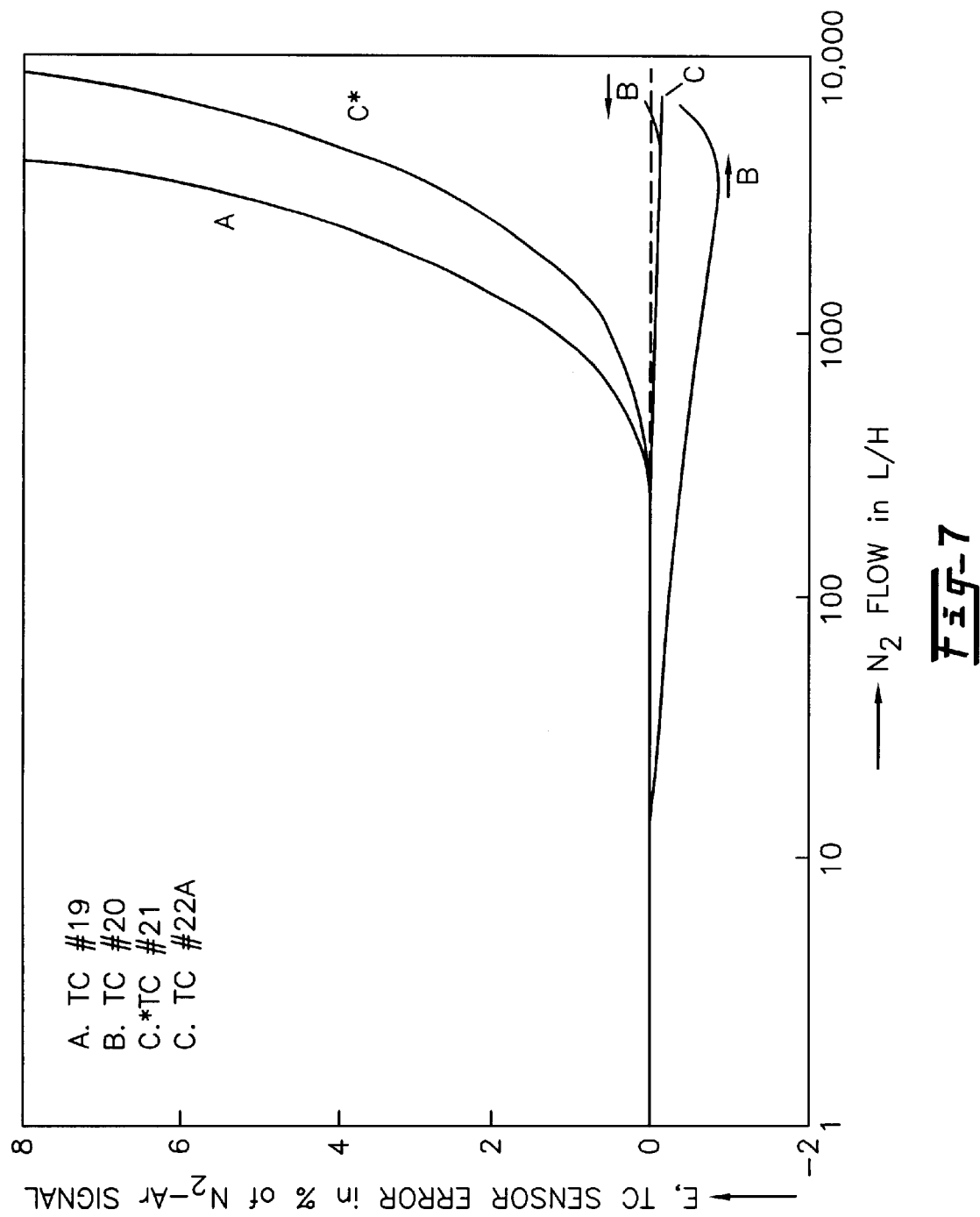
FIG. 7 is a graph showing the sensitivity of sensor in terms of output to flow velocity for several protection barriers.

FIG. 7 shows the results of sensitivity to flow for microsensor housings of FIGS. 4a, 4b and 4c. At this time, FIG. 4c represents our preferred embodiment, also from the point of view of ease of assembly, whereby the sensor housing and baffle are machined out of one piece. Electronics 28 (as shown, for example, in FIG. 4d) can be fastened within an enclosure having a cover 29 of FIG. 4e. For protection of electronics 28 against humidity, o-ring seals 30 are used on the chip holder.

In FIG. 4e, barrier 25 has six holes 21 having a diameter of about 0.050 inch. The diameter of a circumference of a perimeter touching the outside edges of holes 21 is about 0.170 inch, and diameter 57 of a circumference of a perimeter touching the inside edges of holes 21 is about 0.070 inch. The spacing between adjacent holes 21 is about 0.010 inch. A thickness 75 of barrier 25 at its center is about 0.030 inch. The curvature of baffle 25 is outward towards sensor 11. The entrance of inlet 64 has a diameter 65 of about 0.430 inch. A length 66 of inlet 64 from the entrance to the center of barrier 25 is about 0.510 inch. Diameter 19 of barrier 25 at the upper end of inlet 64 is about 0.190 inch. Distance 76 between chips 11 and the center of barrier 25 is about 0.030 inch. The diameter of sensor 11 is about the same as diameter 57 of the solid portion at the center of barrier 25.

Sensitivities to flow and to flow turbulence were measured with the same setup mentioned above (18 mm ID pipe and sensor chip position at 24 mm from pipe 31 center), except that the flow was increased from 2 to 10,000 L/h (0.0333 to 167 L/min, or 0.22 to 1092 cm/s, with Re=2.7 to 13,600). In one modified setup, in which the gas supply from pressurized tanks and regulators was replaced with a shop vacuum pump, the effect of turbulence was striking. Without measurable pressure fluctuations ($\Delta p \leq 0.3$ cmWC), the random motion of turbulence enhanced the heat transfer at the site of the chip's sensor elements to the point of simulating the behavior of a fluid with higher than actual thermal conductivity. The magnitude of the resulting error under those conditions could be as large as the thermal conductivity change between Ar and $N_2$, indicating that the provided sensor protection was insufficient. Even under mild flow conditions (Re<10,000), FIG. 7 shows that the sensor housings shown in FIGS. 4a–c, and 4e with convection barriers in the form of a wire screen 33, louvers 32 and a baffle 25, respectively, do differ significantly in their protection effectiveness.

Screen 33, if its mesh is tight enough to protect against flow and turbulence, exhibited long response times ($\tau_{63\%}$=20 (or 4) seconds for setup 34 indicated in FIG. 4d) and clogged within a few months of operation as represented by curve A.

Louvers 32 (FIG. 4b and curves $\vec{B}$ and $\overleftarrow{B}$ in FIG. 7) provided better protection and did not clog, but had a still longer response time; but baffle 25 (FIGS. 4c, 4e, and and 4f) provided excellent protection, did not clog and exhibited response times of 0.34 and 3.5 seconds. Curves $\vec{B}$ and $\overleftarrow{B}$ represent the opposite flow directions during the tests. Curve C* in FIG. 7 corresponds to a sensor housing 100 with a baffle constructed similarly to baffle 25 of FIG. 4f, except that it had a set of holes 21 about two times larger than those in FIG. 4e, which made sensor housing 100, with about a two times larger chip cavity 22, still respond rapidly, but was too sensitive to flow 16. All of the data shown in FIG. 7 were measured under the setup 34 conditions, with reference to FIG. 4d, where the flow rate was 4 L/min, the inside diameter of the tube was 18 mm and normal distance from the center of tube 31 to the sensor 11 was about 24 mm.

The effect of condensation and the recovery thereof was quantified with the help of a gas-tight enclosure 37 in which sensor 11 and its support structure 35 could be held above a liquid pool 38 of heptane, and stabilized at a temperature of 10–12 degrees C below that of the saturated vapor in equilibrium with the liquid. Setup 36 is shown in FIG. 8b. However, such condensation tests took several hours, and at times days, to complete. A faster, and also more repeatable test, consisted of dropping 1.6 mg heptane droplets 39 and letting them fall through convection barrier 25 onto sensor 11. This test version may represent a worst-case condensation scenario, i.e., when condensate in the form of a droplet 39 impinges on the sensitive surface of a sensor 11.

Figure 8A:
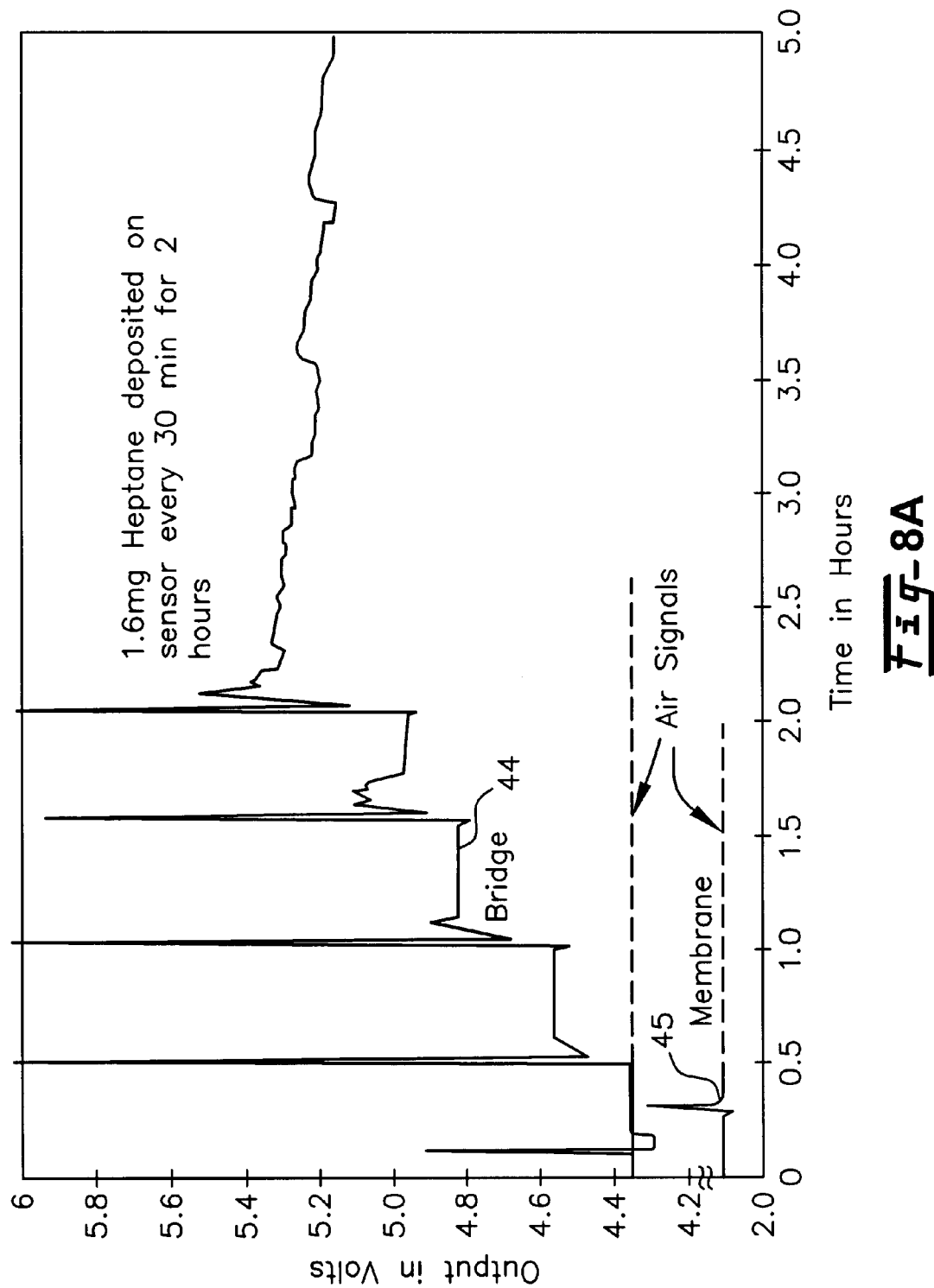
FIGS. 8a and 8b are a graph of droplet test results for the present housing barrier and microbridge sensor chip, and the setup for the condensation tests, respectively.
Figure 8B:
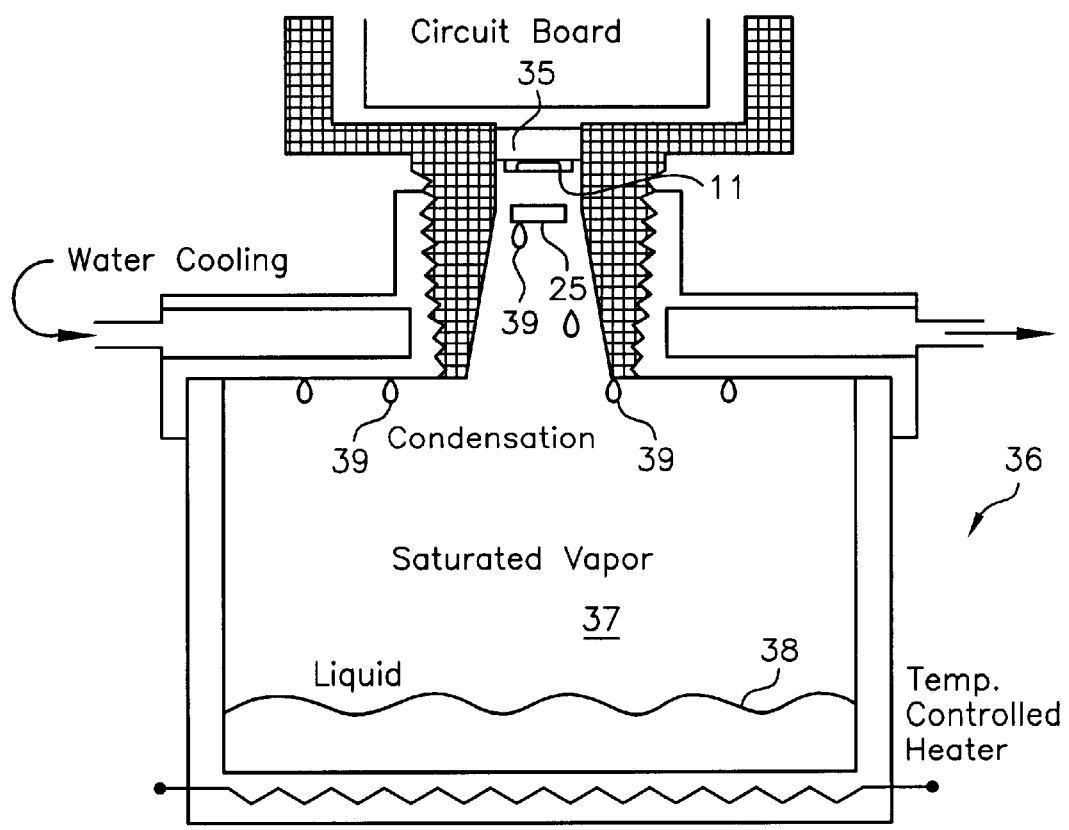

As shown in curve 44 "bridge" of FIG. 8a for test results with an "open" microbridge sensor structure 40 (see FIG. 10a), each 1.6 mg droplet, deposited in intervals of 30 minutes, shifted the sensor output signal by an additional amount, which then does not return for several hours to the original value. Under a microscope, one could see that a small quantity of liquid had lodged itself under the microbridge, where capillary action kept it, in spite of the volatility of heptane (eventually it was removed with a still more volatile solvent, such as acetone).

Figure 9:
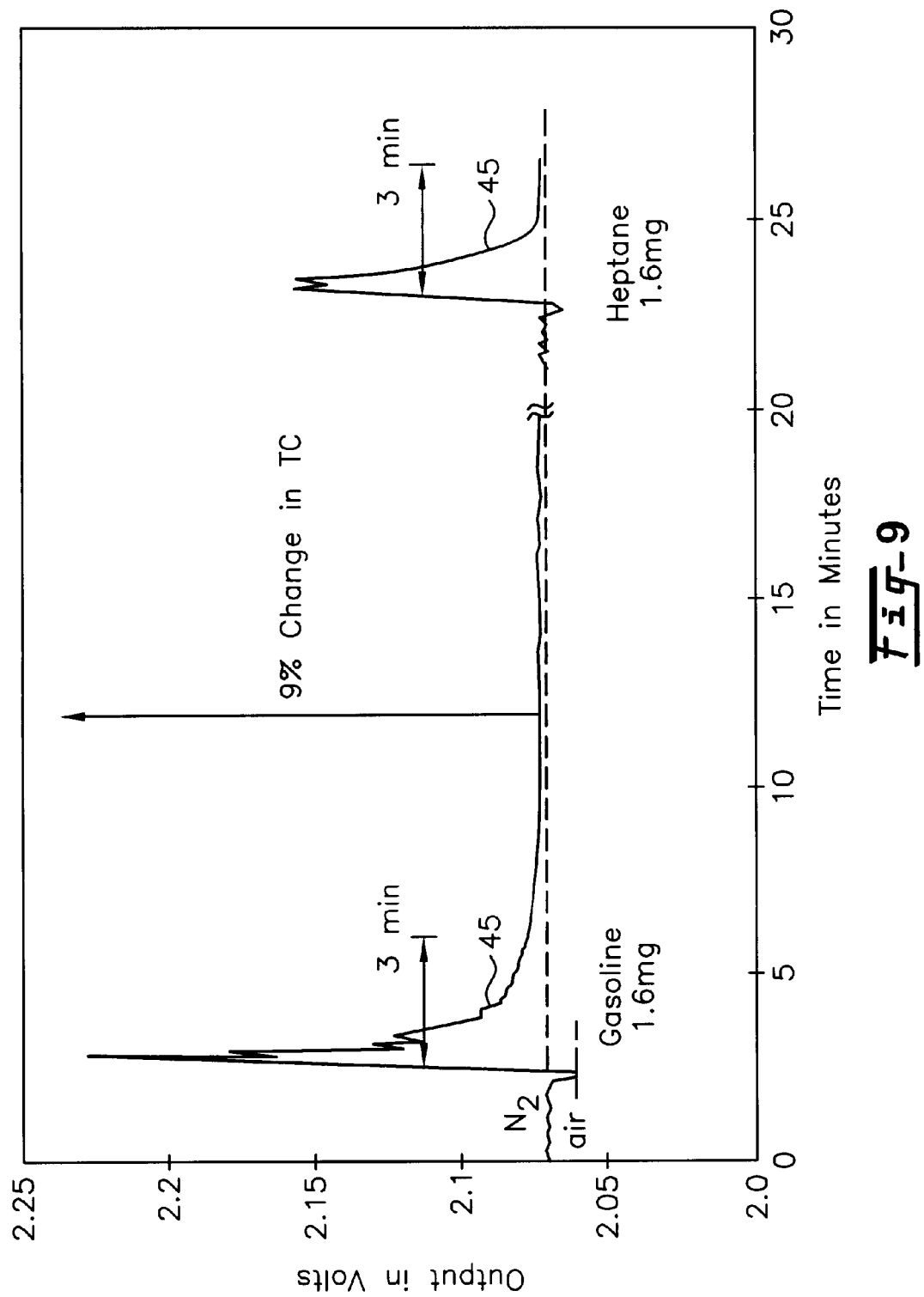

In view of this insight, the droplet test was repeated with a closed micromembrane structure 41 (FIG. 10b), and the results were plotted in curve 45 "membrane" of FIG. 8a. As shown, the initial effect of the droplet is similar to that of curve 44 "bridge", causing the signal to rise to indicate the presence of a higher thermal conductivity fluid. But within three minutes (see curve 45 "membrane" or a redrawn version of it on an expanded scale in FIG. 9), the signal had largely returned back to the original level.

Four variations in sensor chip design were used, as presented in FIGS. 10a, 10b, 10c and 10d. They all share the Pt thin-film resistive heater 46 and sensing elements 47 and the silicon nitride passivation 48 of these elements, but differ in the size, shape and support of this high surface-to-volume sensing structure.

Figure 10A:
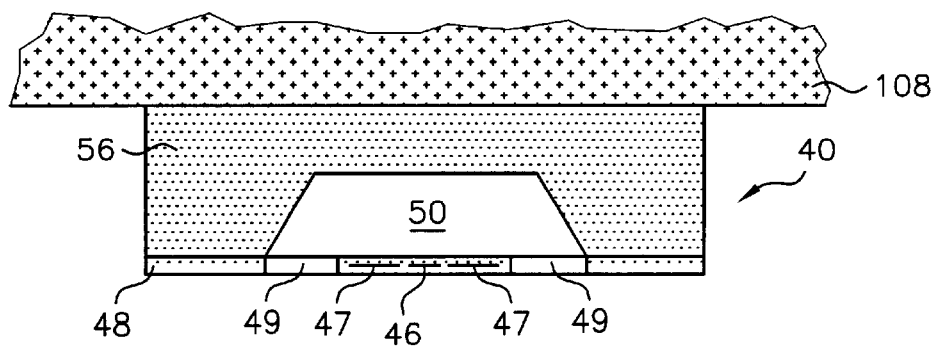
FIGS. 10a–10g show various sensor microstructures.
Figure 10B:
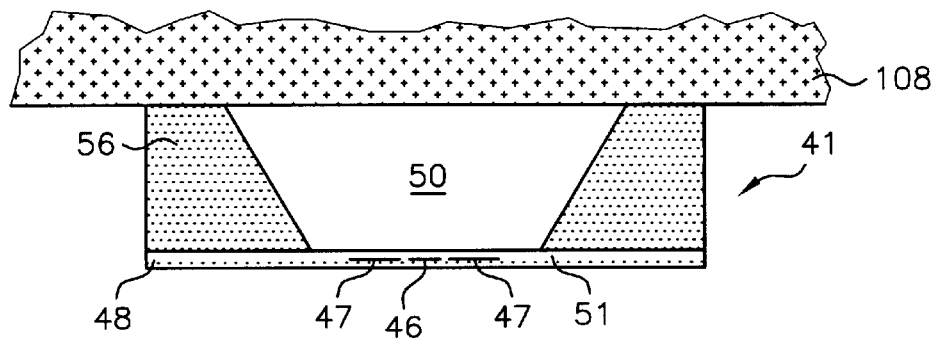
Figure 10C:
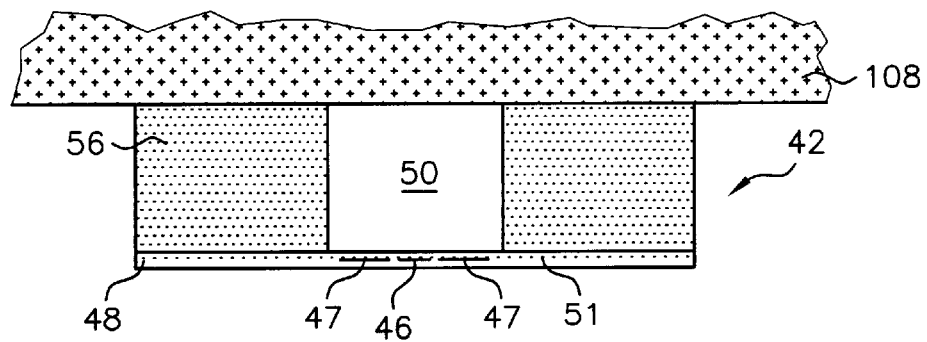
Figure 10D:
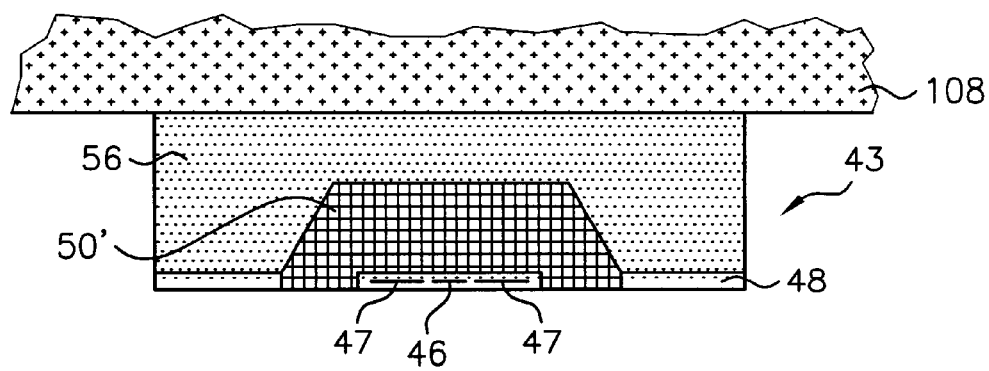

FIG. 10a shows the standard, off-the-shelf microbridge sensor structure 40, depicted in FIG. 1c and manufactured since 1987. FIG. 10b reveals a sealed, square micromembrane 51 of sensor structure 41 of about 750 $\mu$m (0.030") on the side. Micromembrane 51 covers and seals open areas 49 shown in structure 40 to seal and prevent liquid or other substances from being lodged under the bridge supporting heater 46 and sensing elements 47 etched over open volume 50. FIG. 10c shows a similar version of sensor structure 41, except that micromembrane 51 is circular and of 500 $\mu$m (0.020") in diameter. FIG. 10d reveals a polymer-filled volume 50' of structure 43, which is like structure 40, wherein the microbridge of heater 46, sensing elements 47 and filled volume 50', has become part of a solid and robust structure.

The use of ruggedized microsensor 43 via an epoxy fill reduces the effect of dust and droplets 39. The use of micromembrane 51 versus microbridge structure 40 eliminates the condensation problem (no recovery with the microbridge). The use of ruggedized structure 43 (FIG. 10d) increases the range of the sensor to higher flows.

Figure 10E:
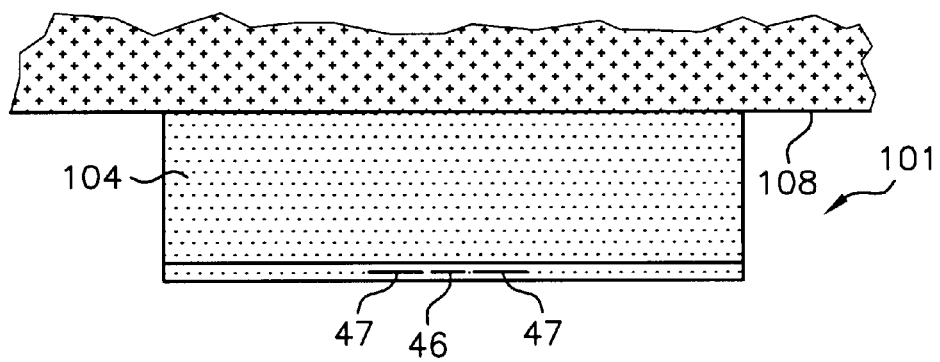
Figure 10F:
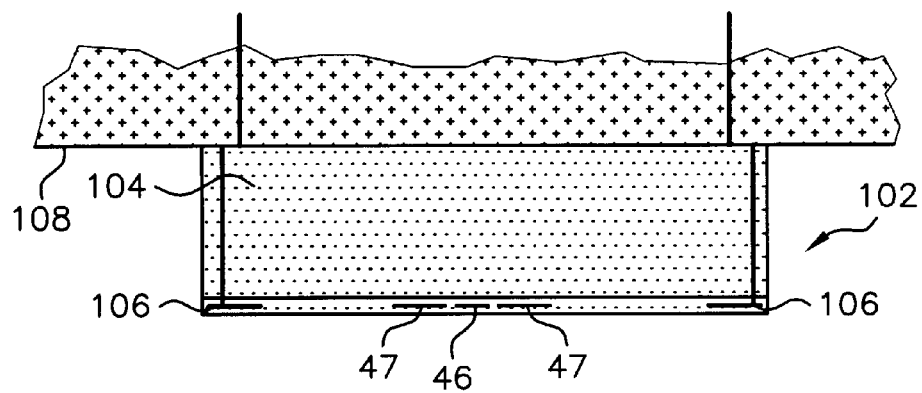
Figure 10G:
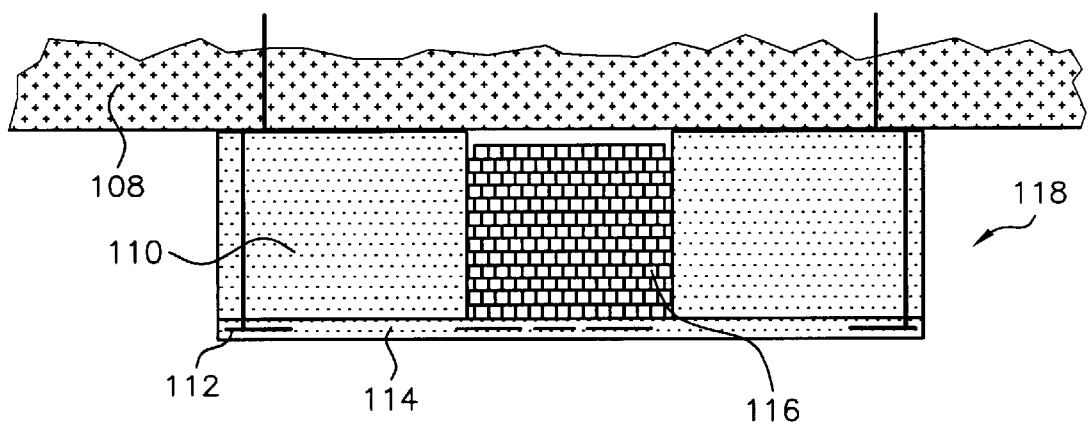

FIG. 10e shows an alternate ruggedized sensor structure 101, whereby the semiconductor body of the sensor is replaced with an electrically and thermally insulating material 104 such as ceramic, metal oxide, or glass, rather than silicon. Pyrex would be a preferred glass because it has a matching thermal coefficient of expansion (TCE) to that of silicon. According to the structure 101, the heaters 46 and sensing elements 47 are deposited on the bulk insulating material 104, thus no recess need be etched and filled with epoxy. In a related structure 102 of FIG. 10f, and in order to increase the sensor's "ruggedness" a further step, the traditional external and therefore breakable wire contacts 106 have been replaced by conducting paths through and internal to the above insulating material 104 and directly to the substrate 108 of the sensor structure. A structure 118 of even greater ruggedness and sensitivity, featuring a sensing membrane 114 supported by a solid, TCE-matched, porous, low thermal conductivity structure 116 is shown in FIG. 10g. The low thermal conductivity structure may be comprised of high density lead oxide glass, porous materials such as silica gels, metal oxides and zeolites, or composite materials such as glass frits. This sensor structure 118 may also include internal conducting paths 112 through the insulating material 110 to substrate 108 as previously described.

Figure 13A:
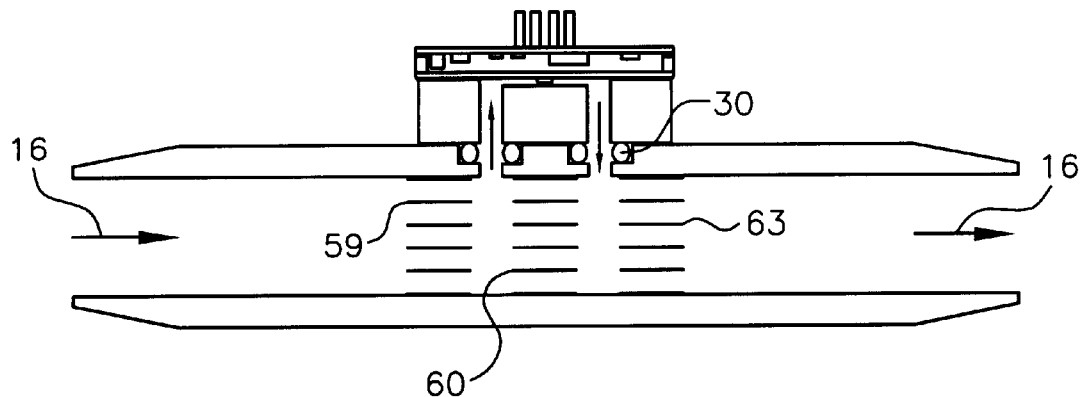
FIGS. 13a and 13b show a bypass flow thermal property microsensor having honeycomb flow straighteners or "screens" in the main flow region.
Figure 13B:
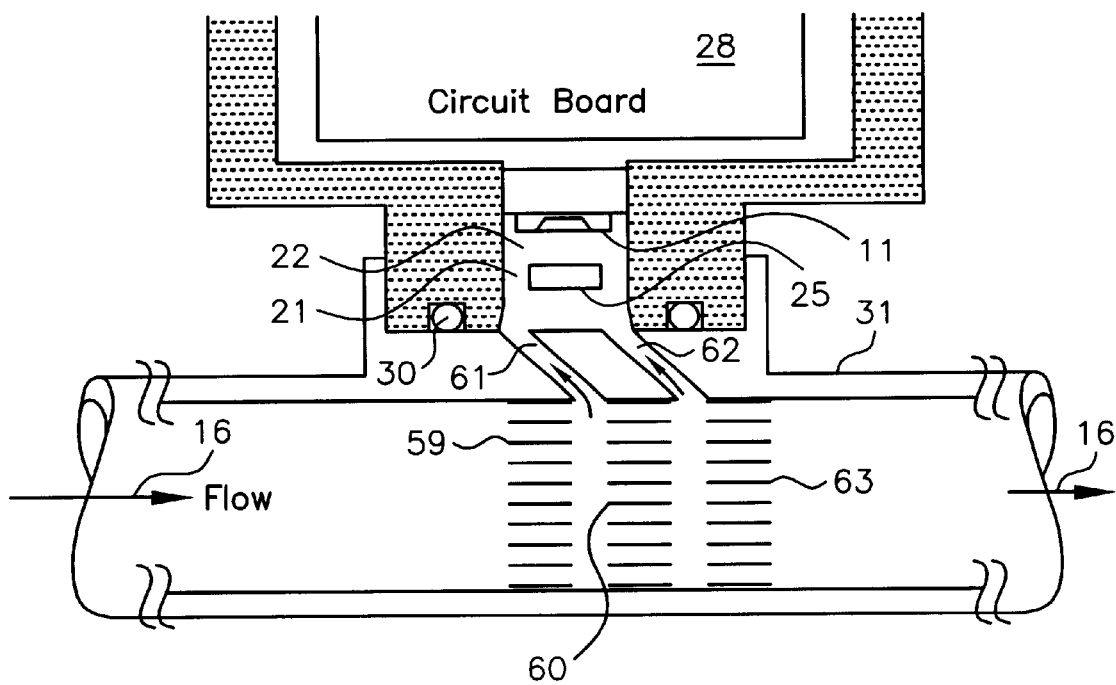
Figure 13C:
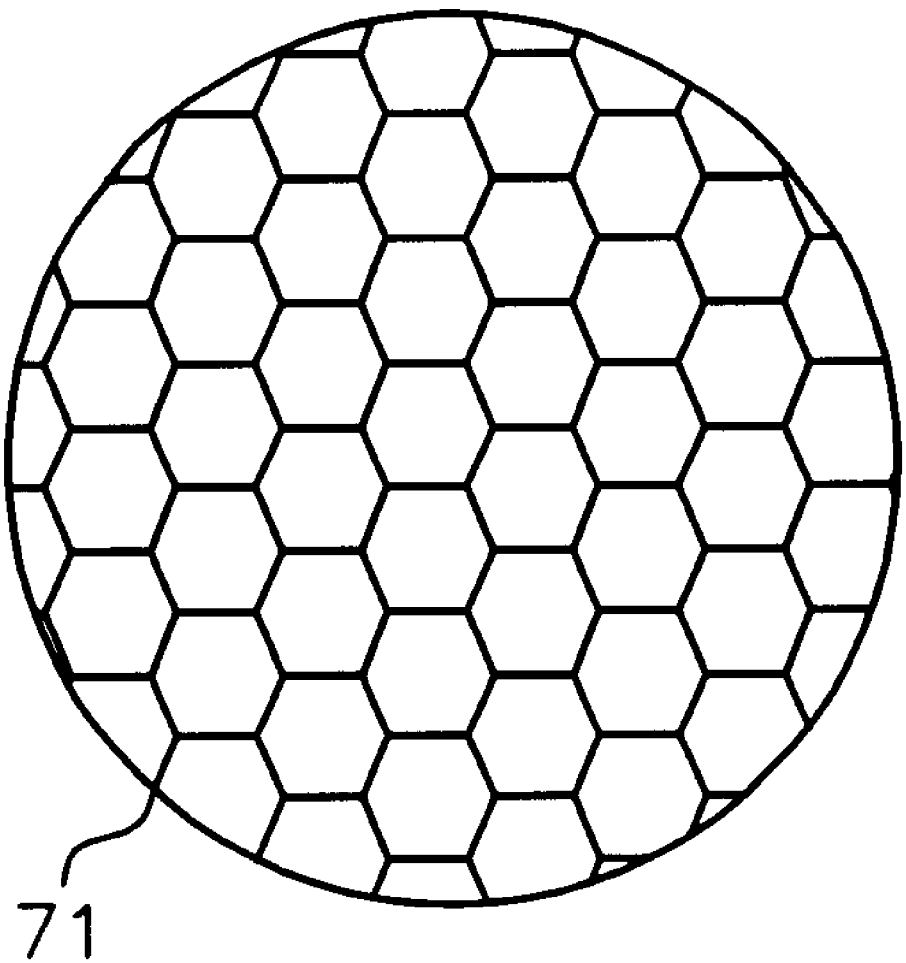

FIG. 13a shows honeycomb screens 59, 60 and 63 used in a bypass flow microsensor for gases and liquids. End view 71 shows an example of a honeycomb design of the screens. In FIG. 13b, the use of a special bypass 58 to baffle 25 of sensor 11 reduces particle collection on the sensor 11 surface in FIG. 13b. Honeycomb screen 59 faces flow 16 to calm down turbulence. Honeycomb screen 60 then tends to force, by flow restriction and a tortuous path to the sensor inlet, a part of flow 16 with convection up through an offset bypass 61 up to baffle 25 having holes 21. The reduced flow makes for a lower influence of turbulence. The tortuous path makes it difficult for heavier particles to flow into the volume about baffle 25. Baffle 25 is the convection barrier, and diffusion of the fluid occurs in volume 22. Fluid is forced down a bypass channel 62 into pipe 31, and joins flow 16 through another honeycomb screen 63. The driving force of the fluid into and out of bypass channels 61 and 62, respectively, is provided by the pressure drop across screen 60 only.

Figure 14A:
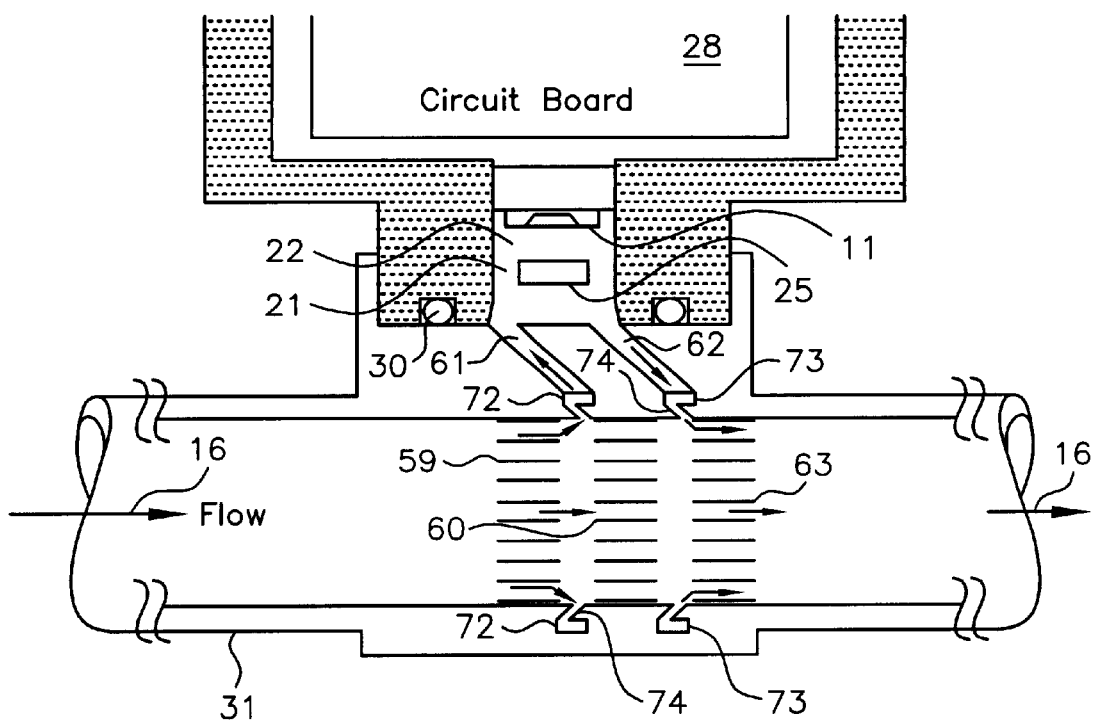
FIG. 14a reveals a bypass flow thermal property microsensor having piezometric sampling.
Figure 14B:
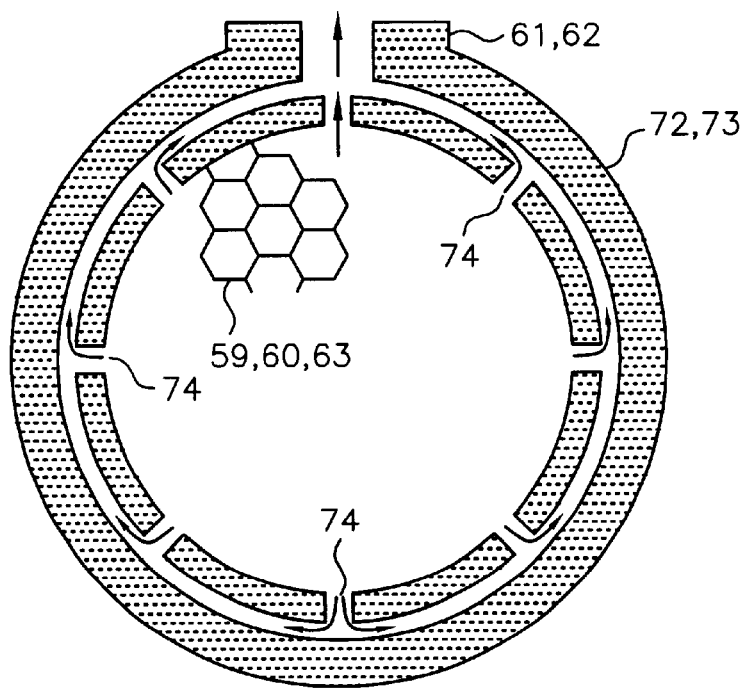
FIGS. 14b and 14c show flow channel cross-sections of alternate multiport piezometric sampling devices.
Figure 14C:
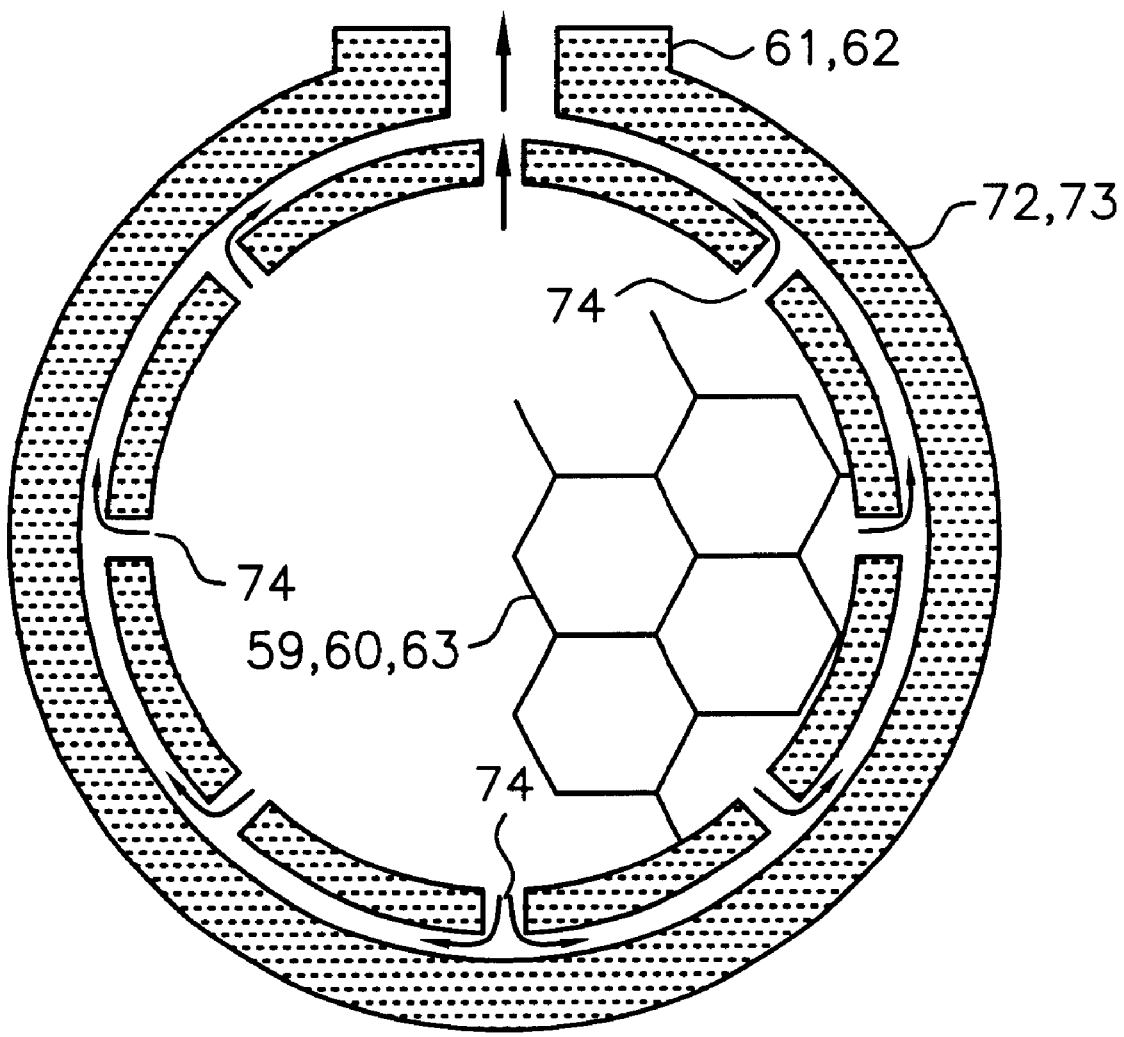

FIG. 14a shows a configuration like that of FIG. 13b except it has multiple port (i.e., piezometric) sampling devices 72 and 73, which are channels around the main fluid conveyance mechanism or pipe 31 with a half of a dozen or more ports 74 from pipe 31 to the respective channel around the pipe. From device 72, fluid goes to bypass channel 61, to barrier 25 and returns back into pipe 31 via bypass channel 62, to device 73 and ports 74. Devices 72 and 73 reduce and average the effects of noise and the turbulent effects of flow 16 upon the convection of fluid into the volume about convection barrier 25. FIG. 14b shows a flow channel cross-section of a multiport piezometric sampling device 72, 73. Examples of two sizes of a honeycomb for screens 59, 60 and 63 are illustrated in FIGS. 14b and 14c. Flow velocity and pressure to the channels, among other things, determine the selection and sequence of screen sizes. In FIGS. 13a, 13b and 14a, O-ring seals 30 are used to seal the connection of the thermal property sensor to fluid conveyance or pipe 31.

Table 1 shows aspects of structures 40, 41, 42 and 43. Among these stands out the tradeoff one makes to eliminate the interference by condensation and switching to a micromembrane 51 structure 41, 42 or 43. The second column in Table 1 lists the unamplified thermal conductivity (TC) sensor signals resulting from switching from $N_2$ to Ar, corresponding to a drop of 30.8% in TC. As shown, the TC mV signals are lower for the micromembrane 51 structures because only one side of their micromembrane 51 is exposed to the new sample gas, which amounts to an exact factor of two times, as verified with one membrane chip before and after sealing it to its substrate. The fact that micromembrane 51 diameter, thickness and the temperature coefficient of resistance of the Pt thin-film resistive heater 46 also influence these signals accounts for the listed values, which were measured.

Figure 11A:
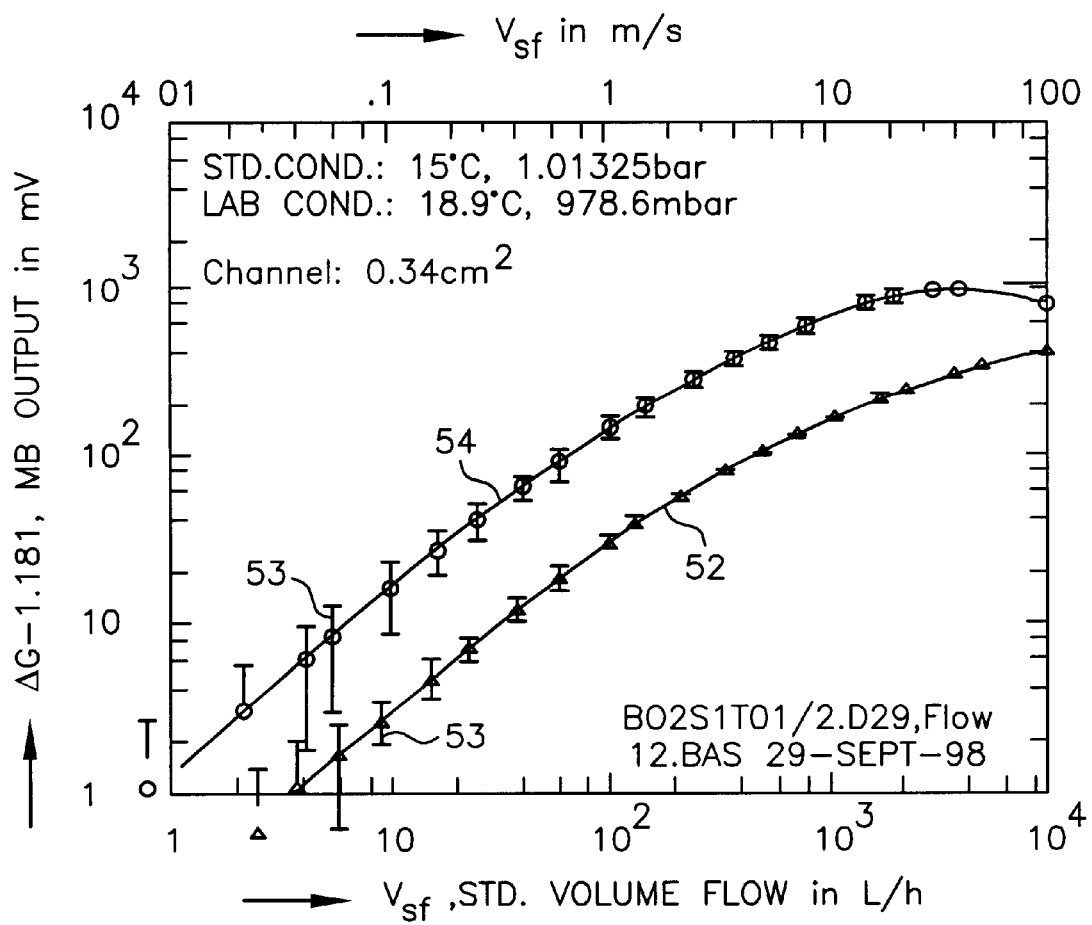
FIG. 11a is a graph of a performance comparison between a standard and a ruggedized flow microsensor.

The bottom row in Table 1 for structure 43 represents the results for a standard microbridge sensor except that its etched-out cavity 50 was refilled with epoxy. The rationale for doing this was the desire to sense high mass fluxes or velocity flows, as e.g., with liquids, whereas manufactured microbridge flow sensor structures 40 saturate at an air velocity near 30 m/s. It has been previously shown that the high limit of this range can be extended by either sensing the heater power as in classical hot-wire anemometry as shown in FIG. 3 (with its consequences of shortened low-flow range and reduced stability), or by increasing the thermal conduction of the heater 46. With the ruggedized structure 43 (Table 1), such an approach was checked out. The experimental flow sensor data, plotted as curve 52 in FIG. 11a, show that by filling-in recess 50 of the microbridge chip with epoxy (triangle points), in structure 43, the desired effect of extending the high limit of measurable gas flows to beyond 100 m/s (upper limit of our calibration rig at the time) is achieved. Curve 54 is similar data of structure 40. And while a drop was expected in signal (two times for the bridge-to-membrane effect plus thermal conduction losses in the sensor itself), the measured four times drop came with the finding that for a given flow, the S/N ratio was not reduced but increased by about 10–20 percent. This is attributed to the increased time constant and associated reduction in sensitivity to turbulence, as indicated by the error bars 53 in FIG. 11a.

Figure 11B:
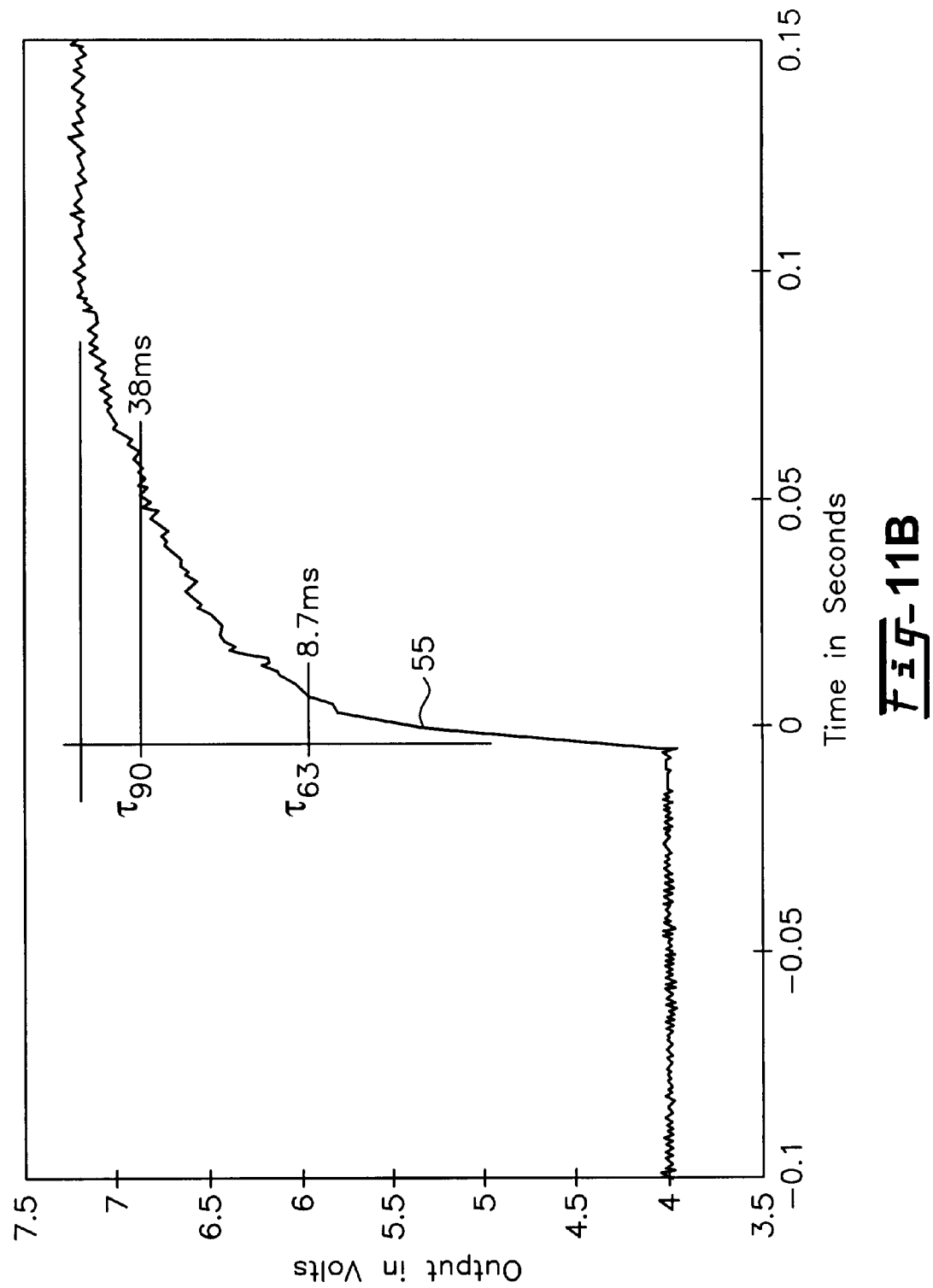
FIG. 11b is a graph of the response time constant of a ruggedized microbridge flow sensor.
Figure 12:
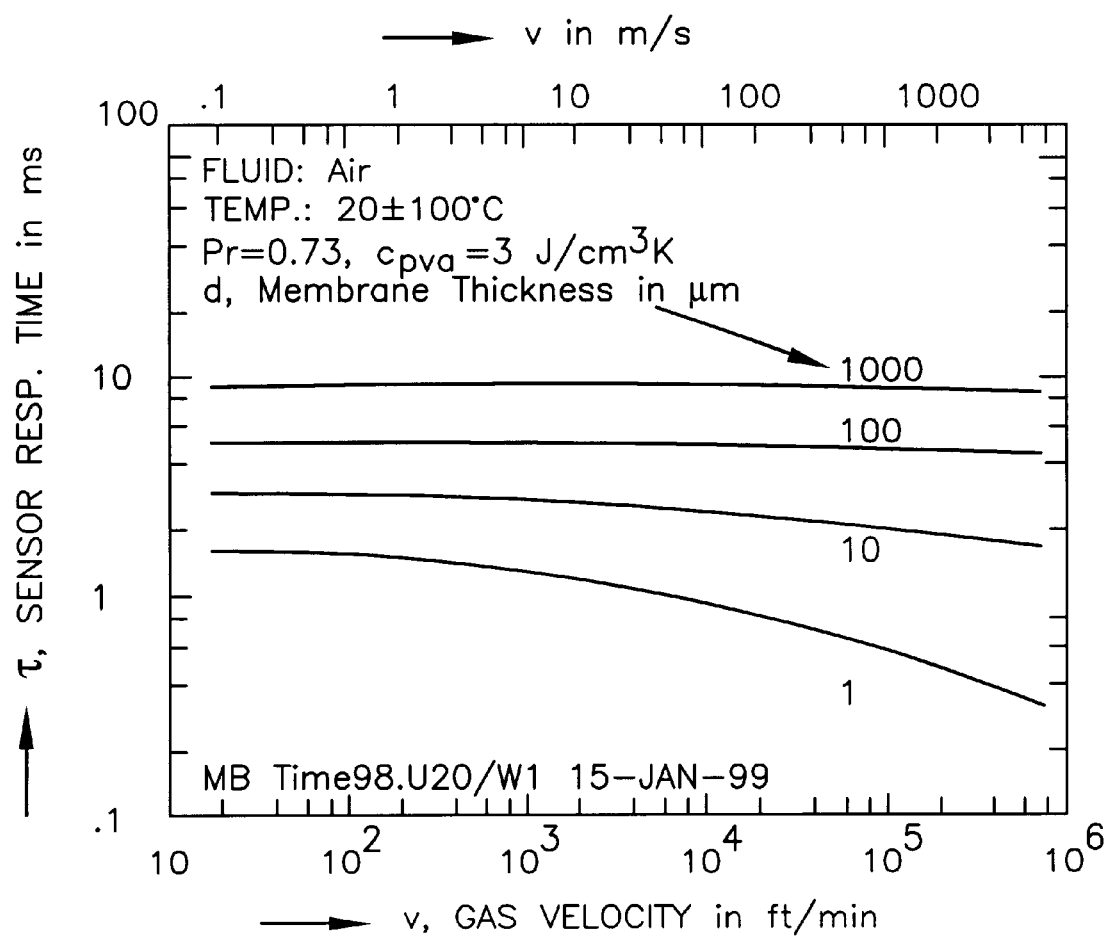
FIG. 12 is a graph revealing the influence of membrane thickness on the response time of a ruggedized microbridge flow sensor.

The draconian remedy of an epoxy fill did not negate the sensitivity benefits of a nimble, 1 $\mu$m-thick sensing structure 43. In fact, performance data of structure 43, plotted as curve 55 FIG. 11b, show that the measured response time of 8.7 ms is still faster than what many applications require.

To summarize, one might recommend sensor structure 40 for top sensitivity applications; sensor structure 42 for sensitive measurements under conditions of high dust load and probability of condensation; and sensor structure 43 for situations where high mass fluxes need to be sensed, regardless of dustload or condensation. Sensor structures 40 and 43 offer the additional feature of being inherently immune to overpressures.

Dust and particulates, if allowed to settle on the chip's sensing elements 47, can alter the heat transfer characteristics, the sensitivities of elements 47 and thus the output signal of sensor 11. There are at least two ways to reduce the probability of particle deposition on the sensing elements 47 surfaces. First one can increase the cross section of the flow channel at sensor 11 (with or without a bypass) to reduce the average particle mass flux at the chip level. Second, one can cleverly design the bypass geometry or the flow path to take advantage of the higher inertia of particles, such that the probability of having microbridge surface 51 in their path is reduced.

For example, for a specified "20-year" aerosol mass flux (in g/cm$^2$) past sensor 11, when sensor 11 is positioned as in present flow channel configuration, one might ask how much that aerosol flux would be reduced by placing sensor 11 in a bypass channel with only ten percent of the flow rate (cm$^3$/s) and F=50% of the mass flux or flow velocity, beyond F, by virtue of clever design of the bypass geometry. A membrane structure 41, 42 or 43 would therefore be preferable and offer less dust retention.

In order to meet a specified thermal conductivity sensor 11 performance in terms of response time, insensitivity to flow, and service life, a tool kit of parameter groups are selected or adjusted for the design of sensor 10. They include sensor chip design and performance, and the geometries of the convective transport section, the convective barrier and the diffusion transport section of the sensor package or housing.

For the parameters of this tool kit, there are generic as well as quantitative guidelines for the design of microenvironmental protection of (thermophysical property) sensors 11, to meet opposing performance demands for "fast response", "operability in high flows" and "long, reliable service" in field environments. These were characterized by measurable dust loads, occasional condensation and flow turbulence, which had resulted in slow response before due to excessive protection.

By comparing the performance of microbridge structure 40 versus micromembrane sensor structures 41, 42 and 43, one is able to demonstrate rapid sensor recovery after condensation with a sealed micromembrane as in sensor structures 41, 42 or 43, but at the price of dropping the thermal conductivity sensitivity by a factor of about two times (the sealed side of micromembrane 51 is not exposed to the sample fluid), and increasing its sensitivity to changes in absolute pressure, as summarized in Table 1.

Sensor structure 43 has protection against interference by laminar or turbulent flow, changes in absolute pressure, particulates, condensation or even flooding, and protection against bulk-physical or -mechanical harm. The flow range is extended by over a factor of four times, while reducing sensitivity to turbulence and retaining sensor flow response times of under 10 ms.

The recommended approach to achieve fast and reliable property sensor operation is to combine convective macroscopic transport 13 of sample fluid 14 up to the sensor's shield 12 or baffle 25, with diffusive transport inside shield 12 or baffle 25 to sensor 11. The housing of FIG. 4c represents this approach, which performed successfully in our tests. As part of this housing, sensor 11 is mounted facedown, and is protected from direct line of flight of aerosols from flowing fluid 14 to sensor 11.

Ruggedization of sensitive and macroscopically fragile thermal sensing elements 47 may be achieved by filling in the thermal isolation recess 50 (air or vacuum pockets) with solid materials of low thermal conductivity (relative to that of the silicon of support 56), such as suitable epoxies. Based on the results of tests, sensor structure 40 is recommended (FIG. 10 or Table 1) for top sensitivity applications in relatively clean environments; sensor structure 42 for measurements under conditions of high dust load and probability of condensation; and sensor structure 43 for situations where high mass fluxes need to be sensed, regardless of dustload, condensation or overpressure.

Other embodiments of the invention, not disclosed here, do not minimize the spirit of the claimed invention.

TABLE 1

RELATIVE SENSITIVITIES OF THERMAL MICROSENSORS TO TC, p AND FLOW

| | Relative Sensitivities | | | | | | | | |
|---|---|---|---|---|---|---|---|---|---|
| | Th. Cond.Signal Ar vs. $N_2$ | | ±TC Noise $N_2$ | Abs.Press. 2 vs. 1 bar $N_2$ | | Flow Signal* $N_2$ at 7.6 m/s | | ±Flow Noise* $N_2$ | |
| Sensor Chip Structure | mV | % | mV$_{rms}$ | mV | %/bar | mV | S/N | mV$_{rms}$ | cm/s |
| Commercial μbridge 40 | −220 | −30.8 | 0.04 | | 0.16** | 600 | 120 | 5 | 0.33 |
| Large μmembrane 41 | −105 | −30.8 | 0.04 | | 10.0 | | | | |
| Small, strong μmembrane 42 | −170 | −30.8 | 0.04 | | 5.0 | | | | |
| Supported/filled μbridge 43 | −86 | −30.8 | 0.04 | | 0.16 | 150 | 130 | 1.2 | 0.30 |
| Before filling | −351 | −30.8 | 0.04 | | 0.16 | | | | |

Reference conditions: $N_2$ at 15° C. and 1 atm (1.01325 bar); $\Delta T_{htr} \approx 100°$ C. electronic response time, τ(63%) ~0.2 seconds
*Heater temperature rise was set to 30° C., instead of 100° C.
**This value is caused by the pressure-dependence of thermal cond. of $N_2$ itself.

What is claimed is:

1. A sensor and sensor housing comprising:
    sensor means for sensing at least one thermal property of a fluid;
    shield means, proximate to said sensor means, for shielding said sensor means from convection of the fluid that detrimentally affects an accuracy of the sensing the at least one thermal property of the fluid; and
    input means for reducing velocity and conveying a portion of fluid to said shield means.

2. The sensor and sensor housing of claim 1, wherein:
    said shield means is situated more than 50 microns from said sensor means; and
    said shield means has at least one opening.

3. The sensor and sensor housing of claim 2, wherein:
    the at least one opening projects a first volume between said shield means and a surface supporting said sensor means;
    an area of said shield, without any at least one opening, projects a second volume between said shield means and the surface supporting said sensor means; and
    a ratio of the second volume to the first volume is close to or exceeds one.

4. The sensor and sensor housing of claim 3, wherein said sensor means comprises:
    a substrate situated on the surface supporting said sensor means;
    a semiconductor piece formed on the substrate wherein the semiconductor piece has a recess; and
    a thermal sensing element proximate to the recess.

5. The sensor and sensor housing of claim 4, wherein the sensing element is suspended over the recess in a form of a bridge.

6. The sensor and sensor housing of claim 5, wherein the recess contains a thermally isolating material.

7. The sensor and sensor housing of claim 4, wherein the sensing element is situated in a membrane covering the recess.

8. The sensor and sensor housing of claim 3, wherein said sensor means comprises:
    a substrate situated on the surface supporting said sensor means;
    an insulating material; and
    a thermal sensing element proximate to said insulating material.

9. The sensor and sensor housing of claim 8, wherein the sensing element is situated in a membrane.

10. The sensor and sensor housing of claim 8, wherein the insulating material is glass.

11. The sensor and sensor housing of claim 10, wherein the glass is Pyrex.

12. The sensor and sensor housing of claim 8, further comprising:
    a conductor for forming an electrical connection between said sensor means and said substrate, said conductor at least partially disposed within said insulating material.

13. The sensor and sensor housing of claim 8, wherein the sensing element is situated in a thin-film structure supported by the insulating material.

14. The sensor and sensor housing of claim 8, wherein the insulating material is epoxy.

15. The sensor and sensor housing of claim 8, wherein said insulating material is bulk insulating material.

16. The sensor and sensor housing of claim 8, wherein sat insulating material further comprises a low-thermal conductivity material.

17. The sensor and sensor housing of claim 16, wherein said low-thermal conductivity material is a porous frit.

18. The sensor and sensor housing of claim 1, wherein:
    said input means has a first end proxmimate to said shield means and a second end; the second end is an opening that has an area equivalent to a circle having a first diameter; the second end is at a first distance from said shield means, and a ratio of the first diameter to the first distance is close to or greater than one.

19. The sensor housing of claim 1, wherein:
    said input means comprises a fluid flow bypass channel for bypass fluid conveyance; and
    the fluid flow bypass channel is designed such that a first flow velocity of a fluid through the bypass channel is less than a second flow velocity of the fluid of a main fluid conveyance device that said input means is connected to.

20. The sensor housing of claim 19 wherein said sensor means is situated in the fluid flow bypass channel.

21. The sensor housing of claim 20, wherein:
    the bypass channel is approximately parallel to the main fluid conveyance device; and
    fluid flow in and out of the bypass channel has direction changes greater than 90 degrees so that high inertia droplets or particles carried by the fluid have a low probability of following the fluid and thus have a low concentration in the bypass channel.

* * * * *